US012790397B2

(12) United States Patent
Schultes et al.

(10) Patent No.: US 12,790,397 B2
(45) **Date of Patent: *Nov. 10, 2026**

(54) SIALYLATED GLYCOPROTEINS

(71) Applicant: Momenta Pharmaceuticals, Inc., Titusville, NJ (US)

(72) Inventors: Birgit C. Schultes, Arlington, MA (US); Chia Lin Chu, Somerville, MA (US); Laura Rutitzky, Somerville, MA (US); Lynn Zhang, Acton, MA (US); Leona E. Ling, Winchester, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/136,803

(22) Filed: Apr. 19, 2023

(65) Prior Publication Data

US 2024/0052040 A1 Feb. 15, 2024

Related U.S. Application Data

(63) Continuation of application No. 16/688,772, filed on Nov. 19, 2019, now abandoned, which is a continuation of application No. 15/985,288, filed on May 21, 2018, now Pat. No. 11,661,456, which is a continuation of application No. 15/028,917, filed as application No. PCT/US2014/060363 on Oct. 14, 2014, now abandoned.

(60) Provisional application No. 61/891,778, filed on Oct. 16, 2013.

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61P 7/00*** | (2006.01) |
| ***C07K 16/00*** | (2006.01) |
| ***C07K 16/06*** | (2006.01) |

(52) U.S. Cl.

CPC .... *C07K 16/2848* (2013.01); *A61K 39/39516* (2013.01); *A61P 7/00* (2018.01); *C07K 16/00* (2013.01); *C07K 16/06* (2013.01); *A61K 2039/505* (2013.01); *C07K 2317/21* (2013.01); *C07K 2317/41* (2013.01)

(58) Field of Classification Search

None

See application file for complete search history.

(56) References Cited

U.S. PATENT DOCUMENTS

| | | | |
|---|---|---|---|
| 4,859,449 | A | 8/1989 | Mattes |
| 5,047,335 | A | 9/1991 | Paulson et al. |
| 5,068,190 | A | 11/1991 | Horiuchi et al. |
| 5,234,905 | A | 8/1993 | Kolhouse et al. |
| 5,340,453 | A | 8/1994 | Jackson |
| 5,360,817 | A | 11/1994 | von Izstein et al. |
| 5,370,872 | A | 12/1994 | Cryz et al. |
| 5,411,942 | A | 5/1995 | Widmer et al. |
| 5,456,909 | A | 10/1995 | Marsh, Jr. et al. |
| 5,459,031 | A | 10/1995 | Blumen et al. |
| 5,500,342 | A | 3/1996 | Miyamura et al. |
| 5,510,261 | A | 4/1996 | Goochee et al. |
| 5,554,730 | A | 9/1996 | Woiszwillo et al. |
| 5,559,103 | A | 9/1996 | Gaeta et al. |
| 5,567,684 | A | 10/1996 | Ladisch et al. |
| 5,663,355 | A | 9/1997 | Ganem et al. |
| 5,723,583 | A | 3/1998 | Seed et al. |
| 5,753,454 | A | 5/1998 | Lee |
| 5,759,823 | A | 6/1998 | Wong et al. |
| 5,856,143 | A | 1/1999 | Nilsson |
| 5,879,912 | A | 3/1999 | Roth |
| 5,945,322 | A | 8/1999 | Gotschlich |
| 6,030,815 | A | 2/2000 | DeFrees et al. |
| 6,048,707 | A | 4/2000 | Klock, Jr. |
| 6,096,555 | A | 8/2000 | Hermentin et al. |
| 6,132,994 | A | 10/2000 | Tawada et al. |
| 6,156,547 | A | 12/2000 | Roth |
| 6,159,954 | A | 12/2000 | Maruyama et al. |
| 6,180,370 | B1 | 1/2001 | Selick et al. |
| 6,190,522 | B1 | 2/2001 | Haro |
| 6,218,149 | B1 | 4/2001 | Morrison et al. |
| 6,261,805 | B1 | 7/2001 | Wood |
| 6,274,568 | B1 | 8/2001 | Schnaar et al. |
| 6,280,989 | B1 | 8/2001 | Kapitonov et al. |
| 6,284,516 | B1 | 9/2001 | Pollock et al. |
| 6,358,710 | B1 | 3/2002 | Graves et al. |
| 6,399,336 | B1 | 6/2002 | Bayer et al. |
| 6,597,996 | B1 | 7/2003 | Venkataraman et al. |
| 6,946,075 | B2 | 9/2005 | Kopf |
| 7,118,675 | B2 | 10/2006 | An et al. |
| 7,138,120 | B2 | 11/2006 | Laursen et al. |
| 7,364,736 | B2 | 4/2008 | Boyle et al. |
| 7,368,542 | B2 | 5/2008 | Mcintyre |
| 7,465,397 | B2 | 12/2008 | An et al. |
| 7,473,680 | B2 | 1/2009 | Bowe et al. |

(Continued)

FOREIGN PATENT DOCUMENTS

| | | | |
|---|---|---|---|
| AU | 2018207367 | B2 | 2/2024 |
| CA | 2828905 | A1 | 9/2012 |

(Continued)

OTHER PUBLICATIONS

Afonso et al., Biomolecules 6:1-20 (2016) (Year: 2016).*

(Continued)

*Primary Examiner* — Thea D' Ambrosio

(74) *Attorney, Agent, or Firm* — Morgan, Lewis & Bockius LLP

(57) ABSTRACT

Pharmaceutical preparations containing polypeptides having particular sialylation patterns, and methods for the treatment of immune-related thrombocytopenia with such preparations, are described.

8 Claims, 5 Drawing Sheets

Specification includes a Sequence Listing.

(56) References Cited

U.S. PATENT DOCUMENTS 7,655,233 B2 2/2010 Autenreith et al.
8,034,906 B2 10/2011 Borhani et al.
8,278,072 B1 10/2012 Matta et al.
8,524,217 B2 9/2013 Presta et al.
8,546,548 B2 10/2013 Bauer et al.
8,632,773 B2 1/2014 Elkon et al.
8,715,652 B2 5/2014 Bolli et al.
8,772,461 B2 7/2014 Earp et al.
8,932,825 B2 1/2015 Wildt
9,114,179 B2 8/2015 Amphlett et al.
9,127,043 B2 9/2015 Gronke et al.
9,170,249 B2 10/2015 Washburn et al.
9,175,068 B2 11/2015 Bauer et al.
9,217,168 B2 12/2015 Prentice
9,481,902 B2 11/2016 Czabany et al.
9,637,768 B2 5/2017 Choi et al.
9,663,581 B2 5/2017 Washburn et al.
9,725,501 B2 8/2017 Earp et al.
9,809,835 B2 11/2017 Engel
9,890,410 B2 2/2018 Washburn et al.
10,087,236 B2 10/2018 Wong et al.
10,125,189 B2 11/2018 Bauer et al.
10,287,315 B2 5/2019 Choi et al.
10,344,063 B2 7/2019 Huang et al.
10,464,996 B2 * 11/2019 Prod'Homme ......... A61P 25/28
10,668,411 B2 6/2020 Lu et al.
10,836,805 B2 11/2020 Huang et al.
11,078,511 B2 8/2021 Greif et al.
11,098,079 B2 8/2021 Gonzalez et al.
11,352,415 B2 * 6/2022 Prod'Homme ........ C07K 16/00
11,377,485 B2 7/2022 Wong et al.
11,447,789 B2 9/2022 Hall
11,661,456 B2 * 5/2023 Schultes ................ C07K 16/00 424/133.1
11,674,125 B2 6/2023 Anthony
2002/0054878 A1 5/2002 Lowman et al.
2002/0160460 A1 10/2002 Paulson et al.
2003/0157108 A1 8/2003 Presta
2004/0137106 A1 7/2004 Ciccone
2004/0138106 A1 7/2004 Schultz et al.
2004/0210396 A1 10/2004 Fischer et al.
2005/0054832 A1 3/2005 Lazar et al.
2005/0106658 A1 5/2005 Bayer et al.
2006/0030521 A1 2/2006 Bayer et al.
2006/0040353 A1 2/2006 Davidson et al.
2006/0127950 A1 6/2006 Bosques et al.
2006/0252672 A1 11/2006 Betenbaugh et al.
2006/0253928 A1 11/2006 Bakker et al.
2008/0261301 A1 10/2008 Kanda et al.
2009/0041770 A1 2/2009 Chamberlain et al.
2009/0053238 A1 2/2009 Allan
2009/0069232 A1 3/2009 Callewaert et al.
2009/0104603 A1 4/2009 Satomaa et al.
2009/0203550 A1 8/2009 Venkataraman et al.
2009/0226968 A1 9/2009 Betenbaugh et al.
2009/0252749 A1 10/2009 Leister et al.
2009/0258014 A1 10/2009 Laterra et al.
2009/0311732 A1 12/2009 Rossi et al.
2009/0317834 A1 12/2009 Laine et al.
2010/0048456 A1 2/2010 DeFrees et al.
2010/0074885 A1 3/2010 Schiff et al.
2010/0081150 A1 4/2010 Liu et al.
2010/0113294 A1 5/2010 Venkataraman et al.
2010/0129843 A1 5/2010 Parsons et al.
2010/0136599 A1 6/2010 Gandhe et al.
2010/0143969 A1 6/2010 Schwartz et al.
2010/0144553 A1 6/2010 Bosques et al.
2010/0166774 A1 7/2010 Dali et al.
2010/0173323 A1 7/2010 Strome et al.
2010/0189714 A1 7/2010 Ravetch et al.
2010/0240871 A1 9/2010 Raju et al.
2010/0278808 A1 11/2010 Ravetch et al.
2011/0076277 A1 3/2011 Ravetch et al.
2011/0223646 A1 9/2011 Schwartz
2011/0224102 A1 9/2011 Gray et al.
2011/0263828 A1 10/2011 Wong et al.
2011/0280873 A1 11/2011 Presta et al.
2012/0009189 A1 * 1/2012 Kasermann ............. A61P 25/00 530/387.3
2012/0058111 A1 3/2012 Ehlers et al.
2012/0100575 A1 4/2012 Taylor et al.
2012/0295273 A1 11/2012 Washburn et al.
2013/0071390 A1 3/2013 Stadheim
2013/0121991 A1 5/2013 Huille et al.
2013/0216522 A1 8/2013 Huille et al.
2014/0046032 A1 2/2014 Blanche et al.
2015/0071936 A1 3/2015 Mendiratta et al.
2015/0087814 A1 3/2015 Wang et al.
2015/0210753 A1 7/2015 Sarvaiya et al.
2015/0252108 A1 9/2015 Washburn et al.
2015/0361128 A1 12/2015 Rajendran et al.
2016/0024179 A1 1/2016 Warner et al.
2016/0090409 A1 3/2016 Prod'Homme et al.
2016/0102298 A1 4/2016 Czabany et al.
2016/0108450 A1 4/2016 Bhatnager et al.
2016/0153020 A1 6/2016 Ronin
2016/0257754 A1 9/2016 Schultes et al.
2017/0051328 A1 2/2017 Tayi et al.
2017/0283492 A1 10/2017 Ravetch et al.
2017/0320959 A1 11/2017 Swanson et al.
2018/0186847 A1 7/2018 Wang et al.
2018/0305440 A1 10/2018 Sarvaiya et al.
2018/0305725 A1 10/2018 Bhatnager et al.
2018/0327498 A1 11/2018 Schultes et al.
2019/0002542 A1 1/2019 Li et al.
2019/0085064 A1 3/2019 Bauer et al.
2019/0100573 A1 4/2019 Wong et al.
2019/0161533 A1 5/2019 Hannappel et al.
2019/0194303 A1 6/2019 Wong et al.
2019/0271021 A1 9/2019 Kopetzki et al.
2019/0343932 A1 11/2019 Clarsund et al.
2020/0032312 A1 1/2020 Bhatnager et al.
2020/0055921 A1 2/2020 Homme et al.
2020/0087298 A1 3/2020 Bechtold et al.
2020/0087402 A1 3/2020 Schultes et al.
2021/0017563 A1 1/2021 Bhatnager et al.
2021/0040527 A1 2/2021 Bhatnager et al.
2021/0163531 A1 6/2021 Abel et al.
2021/0277438 A1 9/2021 Bhatnager et al.
2021/0353752 A1 11/2021 Arroyo et al.
2022/0056109 A1 2/2022 Bosques et al.
2022/0211849 A1 7/2022 Patil
2022/0267413 A1 * 8/2022 Prod'Homme ........ C07K 16/06
2023/0192814 A1 6/2023 Schaeck
2023/0303984 A1 9/2023 Meador, III
2023/0357813 A1 11/2023 Schaeck
2023/0374062 A1 11/2023 Bhatnagar et al.
2024/0141401 A1 5/2024 Bhatnagar et al.
2024/0167069 A1 5/2024 Bhatnagar et al.

FOREIGN PATENT DOCUMENTS

CN 102292640 A 12/2011
CN 104327180 A 2/2015
CN 107429237 A 12/2017
CO 99006716 5/1999
CO 10056078 8/2008
EP 0798003 10/1997
EP 1038881 9/2000
EP 2227255 A1 9/2010
EP 2233502 A1 9/2010
EP 2271382 1/2011
EP 2403866 1/2012
EP 2821482 A1 1/2015
EP 2996772 3/2016
EP 3004368 4/2016
EP 3017057 5/2016
EP 3118209 1/2017
EP 3237608 11/2017
JP 2002542787 12/2002
JP 2005509403 4/2005
JP 2005535291 A 11/2005
JP 2009503105 A 1/2009
JP 2016504337 2/2016

(56) References Cited

FOREIGN PATENT DOCUMENTS

| | | | | |
|---|---|---|---|---|
| JP | 2016-523539 | | 8/2016 | |
| JP | 2017505624 | A | 2/2017 | |
| JP | 2019-514361 | | 6/2019 | |
| JP | 2023526527 | A | 8/2021 | |
| JP | 2023512323 | A | 3/2023 | |
| KR | 10-0989288 | B1 | 10/2010 | |
| KR | 101667677 | B1 | 10/2016 | |
| NC | 2021/0013926 | | 4/2020 | |
| NC | 2022/0014275 | | 4/2021 | |
| NC | 2022/0018364 | | 5/2021 | |
| NZ | 597651 | A | 7/2012 | |
| RU | 2604811 | C2 | 7/2014 | |
| RU | 2580045 | C2 | 4/2016 | |
| RU | 2698655 | C2 | 8/2019 | |
| RU | 2714209 | C2 | 2/2020 | |
| WO | WO 1998/031826 | | 7/1998 | |
| WO | WO1999/064462 | | 12/1999 | |
| WO | WO2000/065070 | | 11/2000 | |
| WO | WO2001/080884 | | 11/2001 | |
| WO | WO2002/000879 | | 1/2002 | |
| WO | WO2002/076578 | | 10/2002 | |
| WO | WO 2005/049078 | | 6/2005 | |
| WO | WO2005/116221 | | 12/2005 | |
| WO | WO 2007/005786 | | 1/2007 | |
| WO | WO2007/011041 | | 1/2007 | |
| WO | WO 2007/019232 | | 2/2007 | |
| WO | WO2007/055916 | | 5/2007 | |
| WO | WO2007/076032 | | 7/2007 | |
| WO | WO2007/087384 | | 8/2007 | |
| WO | WO2007/117505 | | 10/2007 | |
| WO | WO2008/063982 | A2 | 5/2008 | |
| WO | WO2009/021708 | | 2/2009 | |
| WO | WO2009/048072 | A1 | 4/2009 | |
| WO | WO2009/058564 | | 5/2009 | |
| WO | WO2009/079382 | | 6/2009 | |
| WO | WO 2009/111240 | | 9/2009 | |
| WO | WO2010/057626 | | 5/2010 | |
| WO | WO2010/130756 | | 11/2010 | |
| WO | WO2010/136492 | | 12/2010 | |
| WO | WO2010/138502 | | 12/2010 | |
| WO | WO 2010/138736 | | 12/2010 | |
| WO | WO2010/141855 | | 12/2010 | |
| WO | WO2011/103584 | | 8/2011 | |
| WO | WO2011/127325 | | 10/2011 | |
| WO | WO2011138391 | A1 | 11/2011 | |
| WO | WO2011/149999 | A2 | 12/2011 | |
| WO | WO2011157950 | A1 | 12/2011 | |
| WO | WO2012/017156 | | 2/2012 | |
| WO | WO2012022814 | A1 | 2/2012 | |
| WO | WO-2012113863 | A1 * | 8/2012 | ............ C07K 16/18 |
| WO | WO2012/120125 | | 9/2012 | |
| WO | WO2013/013013 | | 1/2013 | |
| WO | WO2013/120066 | | 8/2013 | |
| WO | WO2013/150138 | A1 | 10/2013 | |
| WO | WO2013/163297 | A1 | 10/2013 | |
| WO | WO2013/164837 | | 11/2013 | |
| WO | WO2014/018747 | | 1/2014 | |
| WO | WO2014/052360 | A2 | 4/2014 | |
| WO | WO 2014/055370 | | 4/2014 | |
| WO | WO2014/179601 | A2 | 11/2014 | |
| WO | WO 2014/184545 | | 11/2014 | |
| WO | WO2014186310 | A1 | 11/2014 | |
| WO | WO2015/001033 | | 1/2015 | |
| WO | WO 2015/001034 | | 1/2015 | |
| WO | WO2015/057622 | A1 | 4/2015 | |
| WO | WO2016/037947 | A1 | 3/2016 | |
| WO | WO2016/102436 | A1 | 6/2016 | |
| WO | WO 2017/181148 | | 10/2017 | |
| WO | WO2018/034346 | A1 | 2/2018 | |
| WO | WO 2018/114878 | | 6/2018 | |
| WO | WO2018114879 | A1 | 6/2018 | |
| WO | WO 2018/131893 | | 7/2018 | |
| WO | WO 2019/126041 | | 6/2019 | |
| WO | WO 2018/046774 | | 3/2020 | |
| WO | WO 2020/077298 | | 4/2020 | |
| WO | WO2020077298 | A9 | 5/2020 | |
| WO | WO2021/159476 | A1 | 8/2020 | |
| WO | WO 2020/215021 | | 10/2020 | |
| WO | WO2021/178682 | | 9/2021 | |
| WO | WO 2021/236765 | | 11/2021 | |
| WO | WO2021/236769 | A1 | 11/2021 | |
| WO | WO 2022/038565 | | 2/2022 | |

OTHER PUBLICATIONS

Dotz et al., JASN 32:2455-2465 (2021) (Year: 2021).*

Radosevich et al., Vox Sanguinis 98:12-28 (2010) (Year: 2010).*

Alberts et al. "Molecular Biology of the Cell" Garland Publishing, Inc. 1994.

Alistair Rogers and Yves Gibon, "Enzyme Kinetics: Theory and Practice," Plant Metabolic Networks, 2009, Chapter 4, pp. 71-103.

Altschul, S. F., Gish, W., Miller, W., Myers, E. W., & Lipman, D. J. (1990). Basic local alignment search tool. Journal of Molecular Biology, 215(3), 403-410.

Anthony, R. M., & Nimmerjahn, F. (2011). The role of differential IgG glycosylation in the interaction of antibodies with FcγRs in vivo. Current Opinion in Organ Transplantation, 16(1), 7-14.

Arnold et al., "The impact of glycosylation on the biological function and structure of human immunoglobulins," Annu Rev Immunol., 2007, 25:21-50.

Arroyo et al., "Hyper-Sialylated IgG M254, an Innovative Therapeutic Candidate, Evaluated in Healthy Volunteers and in Patients with Immune Thrombocytopenia Purpura: Safety, Tolerability, Pharmacokinetics, and Pharmacodynamics," Blood, 2019, 134(Supplement 1):1090.

"Arumugam et al., ""Intravenous immunoglobulin (IVIG) protects the brain against experimental stroke by preventing complement-mediated neuronal cell death,"" Procd Natl Acd Sci., 2007, 104(35):14101-14109".

Ausubel, F. M., Brent, R., Kingston, R. E., Moore, D. D., Seidman, J. G., Smith, J. A., & Struhl, K. (Eds.). (2010). Current Protocols in Molecular Biology. John Wiley & Sons.

Ausubel, F. M., Brent, R., Kingston, R. E., Moore, D. D., Seidman, J. G., Smith, J. A., & Struhl, K. (Eds.). (1995). Current protocols in molecular biology. John Wiley & Sons, Inc.

Baxter International Inc. (Jun. 25, 2012). Baxter announces FDA approval for Gammagard Liquid as a treatment for multifocal motor neuropathy. Retrieved from https://investor.baxter.com/investors/events-and-news/news/press-release-details/2012/Baxter-Announces-FDA-Approval-for-GAMMAGARD-LIQUID-as-a-Treatment-for-Multifocal-Motor-Neuropathy/default.aspx.

Beneduce et al., "Anti-inflammatory Activity of IgG-Fc," Curr Top Microbiol Immunol., 2019;423:35-62.

Benesova et al., "Affinity Interactions as a Tool for Protein Immobilization," In: Magdeldin S, editor. Affinity Chromatography: InTech. 2012;29-46.

Goh and Ng, "Impact of Host Cell Line Choice on Glycan Profile," Critical Reviews in Biotechnology 38(6):851-67 (2018).

Bril et al., "IGIV in Neurology—Evidence and Recommendations," Can J Neurol Sci., 1999, 26:139-152.

Brown et al., "Deoxygenated disaccharide analogs as specific inhibitors of beta 1,4-galactosyltransferase 1 and selectin-mediated turmor metastasis." J. Biol. Chem. 284:4952-4959 (2009).

Burckhardt et al., "Immunoglobulin G subclass distribution in three human intravenous immunoglobulin preparations," Vox Sang., 1989, 57(1):10-14.

Cai et al., "Ensuring the Biological Safety of Plasma-Derived Therapeutic Proteins: Detection, Inactivation, and Removal of Pathogens," BioDrugs 19(2):79-96 (2005).

CAS No. 9003-11-6, Block copolymer of ethylene oxide and propylene oxide, Sigma-Aldrich, retrieved on Dec. 14, 2022, retrieved from URL <https://www.products.pcc.eu/en/cas-numbers/9003-11-6/?list type=list>, 6 pages.

Cats et al., "Correlates of outcome and response to IVIg in 88 patients with multifocal motor neuropathy," Neurology, Aug. 31, 2010, 75(9):818-825.

(56) References Cited

OTHER PUBLICATIONS

Chen, Rui et al. "Glycoproteomics analysis of human liver tissue by combination of multiple enzyme digestion and hydrazide chemistry." Journal of proteome research vol. 8,2 (2009): 651-61. doi:10.1021/pr8008012.
Chintalacharuvu et al., "Treatment of Collagen Induced Arthritis by Proteolytic Enzymes: Immunomodulatory and Disease Modifying Effects," J Rheumatology., Sep. 2001, 28(9):2049-2059.
Clark-Curtiss, J. E., & Curtiss, R. III. (1983). Analysis of recombinant DNA using *Escherichia coli* minicells. In R. Wu & L. Grossman (Eds.), Methods in Enzymology (vol. 101, pp. 347-362). Academic Press. https://doi.org/10.1016/0076-6879(83)01023-0.
Cohn, E. J., Oncley, J. L., Strong, L. E., Hughes, W. L. Jr., & Armstrong, S. H. Jr. (1944). Chemical, clinical, and immunological studies on the products of human plasma fractionation. I. The characterization of the protein fractions of human plasma. The Journal of Clinical Investigation, 23(4), 417-432. https://doi.org/10.1172/JCI101508.
Cohn, E. J., Strong, L. E., Hughes, W. L. Jr., Mulford, D. J., Ashworth, J. N., Melin, M., & Taylor, H. L. (1946). Preparation and properties of serum and plasma proteins. IV. A system for the separation into fractions of the protein and lipoprotein components of biological tissues and fluids. Journal of the American Chemical Society, 68(3), 459-475. https://doi.org/10.1021/ja01207a034.
Coisne et al., "Cutting edge: Natalizumab blocks adhesion but not initial contact of human T cells to the blood-brain barrier in vivo in an animal model of multiple sclerosis," J Immunol., 2009, 182:5909-5913.
Court of Justice of the Andean Community. (n.d.). Intranet. comunidadandina.org [online]. Available no later than Apr. 18, 2019. Retrieved Dec. 21, 2022, from https://intranet.comunidadandina.org.
Crow, Andrew R et al. "Mechanisms of action of intravenous immunoglobulin in the treatment of immune thrombocytopenia." Pediatric blood & cancer vol. 47,5 Suppl (2006): 710-3. doi:10.1002/pbc.20980.
Dalziel et al., "Lectin analysis of human immunoglobulin G N-glycan sialylation," Glycoconj J., Dec. 1999, 16(12):801-807.
Dizon-Maspat et al., "Singe Pass Tangential Flow Filtration to Debottleneck Downstream Processing for Therapeutic Antibody Production," Biotechnology and Bioengineering 109(4):962-970 (2012).
Dodel et al., Intravenous Immunoglobulins as a Treatment for Alzheimer's Disease, Drugs 2010; 70 (5): 513-528.
Donadio, S., Monciardini, P., & Sosio, M. (2003). Analysis of the biosynthetic gene cluster for the polyether antibiotic nanchangmycin. Biochemistry, 85(4), 311-321. https://doi.org/10.1046/j.1365-2958.2003.03571.x.
"Dos Santos et al., ""Kinin B2 receptor regulates chemokines CCL2 and CCLS expression and modulates leukocyte recruitment and pathology in experimental autoimmune encephalomyelitis (EAE) in mice,"" J Neuroinflammation., Nov. 2008, 5:49".
Dotz, V., Visconti, A., Lomax-Browne, H. J., Clerc, F., Hipgrave Ederveen, A. L., Medjeral- Thomas, N. R., Cook, H. T., Pickering, M. C., Wuhrer, M., & Falchi, M. (2021). O- and N-Glycosylation of serum immunoglobulin A is associated with IgA nephropathy and glomerular function. Journal of the American Society of Nephrology, 32(10), 2455-2465. https://doi.org/10.1681/ASN.2020081208.
Edelman, G M et al. "The covalent structure of an entire gammaG immunoglobulin molecule." Proceedings of the National Academy of Sciences of the United States of America vol. 63,1 (1969): 78-85. doi:10.1073/pnas.63.1.78.
El Khoury et al., "Ccr2 deficiency impairs microglial accumulation and accelerates progression of Alzheimer-like disease," Nat Med., 2007, 13:432-438.
"Extended European Search Report in European Appin No. 20792022.4, dated Nov. 10, 2022, 11 pages".
Extended European Search Report for European Application No. 21809062.9, dated Oct. 5, 2024 (7 pages).
Fernandez-Cruz et al., "6th International Immunoglobulin Symposium: poster presentations," Clin Exp Immunol., Dec. 2009, 158(Suppl 1):60-67.
Fokkink et al., "Immunoglobulin G Fc N-glycosylation in Guillain-Barre syndrome treated with intravenous immunoglobulin," Clinical and Experimental Immunology, Dec. 2014, 178(Suppl 1):105-107.
Frankish, "Lancet Asia Medical Forum-call for papers," The Lancet Neurology, Sep. 1, 2008, 7(9):P771.
Freshney, R. I. (Ed.). (1986). Animal Cell Culture: A Practical Approach. IRL Press.
Griciuc et al., "Alzheimer's Disease Risk Gene CD33 Inhibits Microglial Uptake of Amyloid Beta," Neuron., 2013, 78:631-643.
Hickman et al., "Microglial dysfunction and defective beta-amyloid clearance pathways in aging Alzheimer's disease mice," J Neuroscience., 2008, 28(33):8354-8360.
Holland et al., "Differential glycosylation of polyclonal IgG, IgG-Fc and IgG-Fab isolated from the sera of patients with ANCA-associated systemic vasculitis," Biochimica et Biophysica Acta., Apr. 2006, 1760(4):669-677.
Horowitz et al., "Strategies for Viral Inactivation," Current Opinion in Hematology 2(6):484-92 (1995).
Hughes et al., "Intravenous immune globulin (10% caprylatechromatography purified) for the treatment of chronic inflammatory demyelinating polyradiculoneuropathy (ICE study): a randomised placebo-controlled trial," Lancet Neurol., 2008; 7:136-144.
Lijima et al., "Efficacy and availability of intravenous immunoglobulin in chronic inflammatory demyelinating polyneuropathy," Nihon Rinsho., Apr. 2012, 70(4):715-721 (English Abstract Only).
Imashuku, ""High dose immunoglobulin (IVIG) may reduce the incidence of Langerhans cell histiocytosis (LCH)-associated central nervous system involvement,"" CNS Neurol Disord Drug Targets., Nov. 2009, 8(5):380-386 (EnglishAbstract Only).
International Preliminary Report on Patentability for International Parent Application No. PCT/US21/33150, dated Nov. 17, 2022 (6 pages).
International Preliminary Report on Patentability for International Parent Application No. PCT/US2020/028863, dated Jul. 20, 2020 (7 pages).
International Preliminary Report on Patentability for International Parent Application No. PCT/US2021/019607, dated Jun. 15, 2021 (10 pages).
International Preliminary Report on Patentability for International Parent Application No. PCT/US2021/020898, dated Sep. 14, 2021 (8 pages).
International Preliminary Report on Patentability for International Parent Application No. PCT/US2021/057658, dated Feb. 4, 2022 (9 pages).
International Preliminary Report on Patentability for International Parent Application No. PCT/US2021/057659, dated Oct. 27, 2021 (8 pages).
International Preliminary Report on Patentability for International Parent Application No. PCT/US2021/060182, dated May 16, 2023 (7 pages).
International Search Report and Written Opinion in International Application No. PCT/US2021/019607, dated Jun. 15, 2021, 9 pages.
International Search Report and Written Opinion in International Application No. PCT/US2021/033156, dated Nov. 2, 2021, 8 pages.
International Search Report and Written Opinion in International Application No. PCT/US2021/020898, dated Sep. 14, 2021, 7 pages.
International Search Report and Written Opinion in International Application No. PCT/US2021/057658, dated Feb. 4, 2022, 8 pages.
International Search Report and Written Opinion in International Application No. PCT/US2021/057659, dated Oct. 27, 2021, 7 pages.
International Search Report and Written Opinion in International Application No. PCT/US2021/060182, dated May 27, 2022, 6 pages.

(56) References Cited

OTHER PUBLICATIONS

International Search Report and Written Opinion in International Application No. PCT/US2020/028863, dated Jul. 20, 2020, 11 pages.
International Search Report and Written Opinion for International Application No. PCT/US21/33150, mailed Oct. 5, 2021 (9 pages).
Jassal et al., "Sialylation of Human IgG-Fc Carbohydrate by Transfected Rat a2,6-Sialyltransferase," Biochemical and Biophysical Research Communications, 2001, 286:243-249.
Jain et al., "Alpha4betal integrin mediates the recruitment of immature dendritic cells across the blood-brain barrier during experimental autoimmune encephalomyelitis," J Immunol., 2010, 184(12):7196-7206.
Janke and Jong., "Impact of IVIg on the interaction between activated T cells and microglia," Neural Res., 2006, 28:270-274.
Kightlinger et al., "Synthetic Glycobiology: Parts, Systems, and Applications," ACS Synth. Biol. 9:1534-62 (2020).
Klutz et al., "Continuous Viral Inactivation at low Ph Value in Antibody Manufacturing," Chemical Engineering and Processing: Process Intensification 102:88-11 (2016).
Kobata, "Function and pathology of the sugar chains of human immunoglobulin G," Glycobiology, 1990, 1(1):5-8.
Kriegler, M. (1990). Gene transfer and expression: A laboratory manual. W.H. Freeman and Company.
Kumpel et al., "Galactosylation of human IgG monoclonal anti-D produced by EBV-transformed Blymphoblastoid cell lines is dependent on culture method and affects Fc receptor-mediated functional activity," Hum Antibodies Hybridomas., 1994, 5(3-4):143-151.
Kuhn, Bernd et al. "The structure of human α-2,6-sialyltransferase reveals the binding mode of complex glycans." Acta crystallographica. Section D, Biological crystallography vol. 69, Pt 9 (2013): 1826-38. doi:10.1107/S0907444913015412.
Kurnik, "Buffer Exchange Using Size Development, and Industrial Application," Biotechnology and Bioengineering 45(2):149-58 (1995).
Lapointe et al., "IVIg therapy in brain inflammation: etiology-dependent differential effects on leucocyte recruitment," Brain, 2004, 127(Pt 12):2649-2656.
Leontyev et al., "Sialylation-independent mechanism involved in the amelioration of murine immune thrombocytopenia using intravenous gammaglobulin," Transfusion, Aug. 2012, 52(8):1799-805.
Liu et al., "Oriented Immobilization of Proteins on Solid Supports for Use in Biosensors and Biochips: a Review," Microchim Acta 2016; 183;1-19.
Lund et al., "Multiple Interactions of IgG with its Core Oligosaccharide can Modulate Recognition by Complement and Human Fcy Receptor I and Influence the Synthesis of its Oligosaccharide Chains," J Immunol., 1996, 157:4963-4969.
Lundstrom et al., "Blood Plasma IgG Fc Glycans are Significantly Altered in Alzheimer's Disease and Progressive Mild Cognitive Impairment," Journal of Alzheimer's Disease, 2014, 38:567-579.
Malhotra et al., "Glycosylation changes of IgG associated with rheumatoid arthritis can activate complement via the mannose-binding protein," Nature Medicine, 1992, 1:237-243.
Manning, R. (May 5, 2014). Embracing complexity: Understanding IVIg to rationally design novel therapeutics [Conference presentation]. PEGS Boston.
Mayya, Viveka et al. "Quantitative phosphoproteomic analysis of T cell receptor signaling reveals system-wide modulation of protein-protein interactions." Science signaling vol. 2,84ra46. Aug. 18, 2009, doi:10.1126/scisignal.2000007.
Mazourov et al., "The Efficacy of systemic enzyme therapy in the treatment of rheumatoid arthritis," Int J Immunotherapy., 1997, XIII(3/4):85-91.
Meyer et al., "Advances in DNA-Directed Immobilization," Curr Opin Chem Biol. 2014;18:8-15.
Mimura et al., "The influence of glycosylation on the thermal stability and effector function expression of human IgGI-Fc: properties of a series of truncated glycoforms," Molecular Immunology, 2000, 37(12-13):697-706.
Mohammad et al., "Nanofiltration Membranes Review: Recent Advances and Future Prospects," Desalination 356:226-54 (2015).
Morrison, "Transfectomas provide novel chimeric antibodies," Science, 1985, 229(4719):1202-1207.
Morrison, D. A. (1977). Transformation in *Escherichia coli*: Cryogenic preservation of competent cells. Journal of Bacteriology, 132(1), 349-351. https://doi.org/10.1128/jb.132.1.349-351.1977.
Naert et al., "CC chemokine receptor 2 deficiency aggravates cognitive impairments and amyloid pathology in a transgenic mouse model of Alzheimer's disease," J Neuroscience., 2011, 31(16):6208-6220.
National Center for Biotechnology Information (NCBI). (Jul. 16, 2007). Substance record SID 24898182. PubChem. Retrieved Dec. 15, 2022, from https://pubchem.ncbi.nlm.nih.gov/substance/24898182.
National Institutes of Health (NIH). (1991). NIH publication 91-3242. National Technical Information Services.
Negre, E., et al. (n.d.). Training continued for hospital pharmacists [Machine-translated document]. Available no later than Apr. 18, 2019. Retrieved Dec. 21, 2022.
Nguyen et al., "Improved HCP Reduction Using a New, All-Synthetic Depth Filtration Media Within an Antibody Purification Process," Biotechnology Journal 14(1):1700771 (2019).
Nimmerjahn et al., "Anti-Inflammatory Actions of Intravenous Immunoglobulin," Annual Review of Immunology, 2008, 26:513-533.
Nishitsuji et al., "Apolipoprotein E regulates the integrity of tight junctions in an isoform-dependent manner in an in vitro blood-brain barrier model," J Biol Chem., 2011, 286(20):17536-17542.
Ofosu et al., "Plasma-Derived Biological Medicines Used to Promote Haemostasis," Thromb Haemost 99:851-62 (2008).
Palva, I., Lehtovaara, P., Kääriäinen, L., Sibakov, M., Cantell, K., Schein, C. H., Kashiwagi, K., & Weissmann, C. (1983). Secretion of interferon by Bacillus subtilis. Gene, 22(3), 229-235. https://doi.org/10.1016/0378-1119(83)90100-0.
Paulson, J. C., & Colley, K. J. (1989). Glycosyltransferases: Structure, localization, and control of cell type-specific glycosylation. Journal of Biological Chemistry, 264(30), 17615-17618. https://doi.org/10.1016/S0021-9258(19)84926-6.
"Puli et al., ""Effects of human intravenous immunoglobulin on amyloid pathology and neuroinflammation in a mouse model of Alzheimer's disease,"" J Neuroinflammation., 2012, 9:105".
Radosevich, M., & Burnouf, T. (2010). Intravenous immunoglobulin G: Trends in production methods, quality control, and quality assurance. Vox Sanguinis, 98(1), 12-28. https://doi.org/10.1111/j.1423-0410.2009.01226.x.
Raju et al., "Glycoengineering of therapeutic glycoproteins: in vitro galactosylation and sialylation of glycoproteins with terminal N-acetylglucosamine and galactose residues," Biochemistry, Jul. 31, 2001, 40(30):8868-8876.
Ramakrishnan, Boopathy et al. "Structural snapshots of beta-1,4-galactosyltransferase-I along the kinetic pathway." Journal of molecular biology vol. 357,5 (2006): 1619-33. doi:10.1016/j.jmb.2006.01.088.
Ramasamy, Velavan et al. "Oligosaccharide preferences of beta1,4-galactosyltransferase-I: crystal structures of Met340His mutant of human beta1,4-galactosyltransferase-I with a pentasaccharide and trisaccharides of the N-glycan moiety." Journal of molecular biology vol. 353,1 (2005): 53-67. doi:10.1016/j.jmb.2005.07.050.
Ramos-de-la-Pena et al., "Protein A Chromatography: Challenges and Process in the Purification of Monoclonal Antibodies," Journal of Separation Science 2019:doi:10.1002/jssc.201800963.
Sambrook, Fritsch & Maniatis, Molecular Cloning: A Laboratory Manual, Second Edition (1989) Cold Spring Harbor Laboratory Press, Cold Spring Harbor, N.Y.
Sambrook, Fritsch & Maniatis, Molecular Cloning: A Laboratory Manual, Third Edition (2001) Cold Spring Harbor Laboratory Press, Cold Spring Harbor, N.Y.
Samuelsson et al., "Anti-inflammatory activity of IVIG mediated through the inhibitory Fc receptor," Science, 2001, 291:484-486.
Sapsford et al., "Functionalizing Nanoparticles with Biological Molecules: Developing Chemistries that Facilitate Nanotechnology," Chem Rev. 2013;113(3)1904-2074.

(56) References Cited

OTHER PUBLICATIONS

Scallon et al., "Higher levels of sialylated Fc glycans in immunoglobulin G molecules can adversely impact functionality," Mol Immunol., 2007, 44(7):524-1534.
Scielo.org.ve. (Dec. 2006). Fronesis. Retrieved Feb. 10, 2023, from http://www.scielo.org.ve/scielo.php?script=sci_arttext&pid=S1315-62682006000300002&Ing=es&nrm=iso.
Smith, T. F., & Waterman, M. S. (1981). Identification of common molecular subsequences. Journal of Molecular Biology, 147(1), 195-197. https://doi.org/10.1016/0022-2836(81)90087-5.
Steen et al., "Protein Engineering for Directed Immobilization," Bioconjug Chem. 2013;24(11):1761-77.
Sudo et al., "Different IVIG Glycoforms Affect In Vitro Inhibition of Anti-Ganglioside Antibody-Mediated 75*Complement Deposition," PLoS ONE, 2014, 9(9):e107772.
Sutherland, "Filtration Overview: A Closer Look at Depth Filtration," Filtration and Separation 45(8)25-28 (2008).
Trilling et al., "Antibody Orientation on Biosensor Surfaces: a Minireview," Analyst 2013;138(6):1619-27.
Wang et al., "Antibody structure, instability, and formulation," Journal of Pharmaceutical Sciences, Jan. 2007, 96(1):1-26.
Wang, "Instability, stabilization, and formulation of liquid protein pharmaceuticals," International Journal of Pharmaceutics, Aug. 1999, 185(2):129-188.
Warne, "Development of high concentration protein biopharmaceuticals: The use of platform approaches in formulation development," European Journal of Pharmaceutics and Biopharmaceutics, Jun. 2011, 78(2):208-212.
Washburn et al., "High-resolution physicochemical characterization of different intravenous immunoglobulin products," PLoS ONE, 2017, 12(7):e0181251.
"Widiapradj a et al., ""Intravenous immunoglobulin protects neurons against amyloid beta-peptide toxicity and ischemic stroke by attenuating multiple cell death pathways,"" J Neurochem., 2012, 122:321-332".
Wikipedia contributors. (n.d.). Medicine. Wikipedia. Retrieved Dec. 21, 2022, from https://es.wikipedia.org/wiki/Medicamento.
Wong et al., "Sialylated IgG-Fc: a novel biomarker of chronic inflammatory demyelinating polyneuropathy," J Neurol Neurosurg Psychiatry., 2016, 87:275-279.
Sybille Bohm et al. (Seminars in Immunopathology, vol. 34, No. 3, Mar. 22, 2012, pp. 443-453) (Year: 2012).
Hee Jun Cho et al: "Efficient Interleukin-21 Production by Optimization of Codon and Signal Peptide in Chinese Hamster Ovarian Cells", Journal of Microbiology and Biotechnology, vol. 29, No. 2, Feb. 28, 2019 (2019-02-28), pp. 304-310, XP055644468, Korea ISSN: 1017-7825, DOI: 10.4014/jmb.1811.11042.
Lars Kober et al: "Optimized signal peptides for the development of high expressing CHO cell lines", Biotechnology and Bioengineering, John Wiley, Hoboken, USA, vol. 110, No. 4, Jan. 17, 2013 (Jan. 17, 2013), pp. 1164-1173, XP071113992, ISSN: 0006-3592, DOI: 10.1002/BIT.24776.
Yampolsky L. Y. et al. The exchangeability of amino acids in proteins, Genetics, 2005, v. 170, No. 4, pp. 1459-1472, abstract, p. 1465, Table 3.
Pakula A. A. et al. Genetic analysis of protein stability and function. Anna. Rev. Genet. 1989, v. 23, pp. 289-310, pp. 305-306.
Tokuriki N. et al. Stability effects of mutations and protein evolvability, Curr. Opin. Struct. Biol., 2009, v. 19, No. 5, pp. 596-604, pp. 596, 598, 602.
Keskin O. et al. A new, structurally nonredundant, diverse data set of protein-protein interfaces and its implications, Protein Sci., 2004, v. 13, No. 4, pp. 1043-1055, abstract, pp. 1043-1044.
Seffernick J. L. et al. Melamine Deaminase and Atrazine Chlorohydrolase: 98 Percent Identical but Functionally Different, Journal of Bacteriology, 2001, v. 183, No. 8, pp. 2405-2410, abstract.
Witkowski A. et al. Conversion of a β-Ketoacyl Synthase to a Malonyl Decarboxylase by Replacement of the Active-Site Cysteine with Glutamine. Biochemistry, 1999, v. 38, No. 36, pp. 11643-11650, abstract, Table. 1.
Shen J. et al. Single variable domain-IgG fusion: a novel recombinant approach to Fc domaincontaining bispecific antibodies, Journal of Biological Chemistry, 2006, v. 281, No. 16, pp. 10706-10714, p. 10713.
Berry M. J. et al. Substitution of cysteine for selenocysteine in type I iodothyronine deiodinase reduces the catalytic efficiency of the protein but enhances its translation, Endocrinology, 1992, v. 131, No. 4, pp. 1848-1852, p. 1848.
Gasser B. et al. Antibody production with yeasts and filamentous fungi: on the road to large scale?, Biotechnology letters, 2007, v. 29, No. 2, pp. 201-212, p. 208.
Jakubke H.-D et al., Aminokisloty, peptidy, belki [Aminoacids, peptides and proteins], Moscow:Mir, 1985, pp. 92-94.
Mohamed E Hassan et al., Impact of immobilization technology in industrial and pharmaceutical applications / 3 Biotech. Dec. 2019; 9(12):440.
B4GT1_HUMAN, accession No. P15291, Uniprot, entry version 5 published Dec. 11, 2019, obtained from <https://rest.uniprot.org/unisave/P15291?format=txt&versions=215>; cited in PTO-892; hereafter "B4GT1_HUMAN" (Year: 2019).
Bowie et al. (Science, 247:1306- 1310, 1990) (Year: 1990).
Dalakas, Marinos et al., "Subcutaneous IgG for chronic inflammatory demylinating polyneuropathy", The Lancet Neurology, vol. 17, No. 1, Jan. 2018 (Jan. 2018), pp. 20-21, XP085320330, ISSN: 1474-4422, DOI: 10.1016/S1474-4422 (17) 30379-4.
Deb et al. Bacterial expression, correct membrane targeting and functional folding of the HIV-1 membrane protein Vpu using a perplasmic signal peptide, PLOS ONE, published Feb. 22, 2017, vol. 12, No. 2 (Year: 2017).
DeStefano, A., & Hunt, D. (2012). US Pharmacopeia Proposes New Standard on Glass Quality. Pharmaceutical Technology, 68-70. PharmTech.com/usp (Year: 2012).
Devos et al., Practical limits of function prediction. Proteins: Structure, Function, and Genetics. 2000, vol. 41: 98-107. (Year: 2000).
Gevaert et al., Gel-Free Proteomics: Methods and Protocols, Humana Press, Ch 20, pp. 299-308 (Year 2011).
Gramer et al. (Biotechnical Bioeng. Jul. 2011;108(7):1591-602. doi: 10.1002/bit.23075. Epub Feb. 18, 2011) (Year: 2011).
Harrus et al., The dimeric structure of wild-type human glycosyltransferase B4GalT1, PLOS ONE, published Oct. 23, 2018, vol. 13, No. 10 (Year: 2018).
Hawe, A. et al. (2013) Pharmaceutical feasibility of sub-visible particle analysis in parenterals with reduced vol. light obscuration methods. European Journal of Pharmaceutics and Biopharmaceutics, 85(3), 1084-1087 (Year: 2013).
Hopax (The families of biological buffers, obtained from: https://www.hopaxfc.come/en/blog/the-families-of-biological-buffers (Jan. 22, 2019)) (Year :2019).
Ishida (Effects of point mutation on enzymatic activity: correlation between protein electronic structure and motion in chorismate mutase reaction. J Am Chem Soc. May 26, 2010; 132(20):7104-18. doi: 10.1021/ja100744h) (Year: 2010).
Kiese, S., Pappenberger, A., Friess, W., & Mahler, H.-C. (2008). Shaken, Not Stirred: Mechanical Stress Testing of an IgG1 Antibody. Journal of Pharmaceutical Sciences, 97(10), 4347-4366. https://doi.org/10.1002/jps.21328 (Year: 2008).
Kumar et al., "Immunoglobulin therapy in the treatment of multifocal motor neuropathy", J Neurol Sci, 2017, vol. 375, pp. 190-197.
Kurogochi, Masaki et al., "Relative Quantitation of Flycopeptides Based on Stable Isotope Labeling Using MALDI-TOF MS", Molecules, Jul. 9, 2014, vol. 19, No. 7, pp. 9944-9961, DOI: 10.3390/molecules19079944.
Laroy et al., Characterization of sialyltransferase mutants using surface plasmon resonance, Glycogiology, published Mar. 1, 2001, vol. 11, No. 3, p. 175-182 (Year: 2001).
Lazar et al. (Molecular and Cellular Biology. 1988; 8(3): 1247-1252) (Year: 1988).

(56) References Cited

OTHER PUBLICATIONS

LCGC Asia Pacific—Jun. 1, 2007, obtained from: https://www.chromatographyonline.come/view/butter-preparation-hints-tips-and-common-errors-0) (Year: 2007).
Lewis et al. (α-2,3-Sialyltransferase Expression Level Impacts the Kinetics of Lipooligosaccharide Sialylation, Complement Resistance, and the Ability of Neisseria gonorrhoeae to Colonize the Murine Genital Tract. mBio 6:10.1128/mbio.02465-14) (Year: 2015).
Mohapatra et al., Design of Superparamagnetic Iron Oxide Nanoparticle for Purification of Recombinant Proteins. J. Nanosci. Nanotechnol., 2007, vol. 7: 3193-3199 (Year: 2007).
Nagwa teaches that (Question Video: Identifying Possible Effects of a Mutation on the Active Site of an Enzyme, obtained from: http://web.archive.org/web/20210120131812/https://www.nagwa.com/en/videos/450142461549/, available as of Jan. 29, 2021 as evidenced by Wayback Machine) (Year: 2021).
Olczak et al., Comparison of different signal peptides for protein secretion in nonlytic insect cell system, Analytical Biochemistry, published 2006, vol. 359, p. 45-53 (Year: 2006).
Ritter, Christian et al., "Chronic inflammatory demyelinating polyneuropathy (CIDP): change of serum IgG dimer levels during treatment with intravenous immunoglobulins", Journal of Neuroinflamation, Biomed Central Ltd., London, GB, vol. 12, No. 1, Aug. 14, 2015 (Aug. 14, 2015), p. 148, XP021228661, ISSN: 1742-2094, DOI: 10.1186/S12974-015-0361-1.
Roy, Rini et al., "Absolute Quantitation of Glycoforms of Two Human IgG Subclasses Using Synthetic Fc Peptides and Glycopeptides", Journal of the American Society for Mass Spectrometry, May 23, 2018, vol. 29, No. 6, p. 1086-1098, DOI: 10.1007/s13361-018-1900-7.
SIAT1_HUMAN, accession No. P15907, Uniprot, entry version 194 published Jan. 16, 2019, obtained from <https://rest.uniprot.org/unisave/P15907?format=txt&versions=194>; (Year: 2019).
Sinha, Sandipan et al., "Comparison of LC and LC/MS methods for quantifying N-glycosylation in recombinant IgGs", Journal of the American Society for Mass Spectrometry, Nov. 1, 2008, vol. 19, No. 11, p. 1643-1654, DOI: 10.1016/j.jasms.2008.07.004.
Soliven B.: "Animal Models of Autoimmune Neuropathy", ILAR Journal, vol. 54, No. 3, Jan. 1, 2014 (Jan. 1, 2014), pp. 282-290, XP093301065, US ISSN: 1084-2020, DOI: 10:1093/ilar/ilt054.
"Glycosylation main approval issue with biosimilars," <http://gabionline.net/Conferences/Glycosylation-main-approval-issue-with-biosimilars>, dated Jan. 9, 2009, retrieved Jul. 18, 2016 (2 pages).
"Scientific Considerations in Demonstrating Biosimilarity to a Reference Product: Guidance for Industry," Food and Drug Administration (2012) (25 pages).
Akiyama et al., "Analysis of the role of glycosylation of the human fibronectin receptor", J. Biol. Chem. vol. 264(30):18011-8 (1989).
Andrade et al., "Solid-phase oligosaccharide synthesis: preparation of complex structures using a novel linker and different glycosylating agents", Org Lett. 1 (11):1811-4 (1999).
Anthony et al., "A Recombinant IgG Fc That Recapitulates the Antiinflammatory Activity of IVIG," Science, Apr. 2008, 320(5874):373-376.
Anthony et al., "Identification of a receptor required for the anti-inflammatory activity of IVIG." Proc Natl Acad Sci USA. 105(50):19571-8 (2008).
Anthony et al., "Intravenous gammaglobulin suppresses inflammation through a novel TH2 pathway." Nature. 475(7354):110-3 (2011) (5 pages).
Anthony et al., "Novel roles for the IgG Fe glycan," Ann NY Acad Sci. 1253(2012):170-80 (2012).
Anthony et al., "Recapitulation of IVIG anit-inflammatory activity with a recombinant IgG Fe." Science. 320(5874):373-6 (2008).
Anthony et al., "Supporting Online Material for Recapitulation of IVIG anti-inflammatory activity with a recombinant IaG Fe," Science. 320: 9 pages (2008).
Anthony et al., "A novel role for the IgG Fe glycan: the anti-inflammatory activity of sialylated IgG Fcs," J Clin Immunol. 30(Suppl 1 ):9-14 (2010).
Arakawa, T et al. "Protein—solvent interactions in pharmaceutical formulations." Pharmaceutical research vol. 8,3 (1991): 285-91. doi:10.1023/a:1015825027737.
Arnold et al., "Human Serum IgM Glycosylation: Identification of Glycoforms That can Bind to Mannan-Binding Lectin," J. Biol. Chem., 2005, 280:29080-29087.
Baker et al., "Metabolic control of recombinant protein N-glycan processing in NSO and CHO cells", Biotechnol Bioeng. 73(3):188-202 (2001).
Barb et al., Supporting Information for "Branch specific sialylation of IgG-Fc Glycans by ST6Gal-I," Biochemistry. 48(41):9705-7 (2009) (8 pages).
Barb, Adam W et al. "NMR characterization of immunoglobulin G Fc glycan motion on enzymatic sialylation." Biochemistry vol. 51,22 (2012): 4618-26. doi:10.1021/bi300319q.
Barsam et al., "Platelet production and platelet destruction: assessing mechanisms of treatment effect in immune thrombocytopenia ", Blood, 2011, 117(21):5723-5732.
Becker et al., "Fucose: biosynthesis and biological function in mammals," Glycobiology. 13(7):41 R-53R (2003).
Bilič G. L. (Ed.) Concise Medical Dictionary (Oxford), vol. 2. Moscow: Veče-AST, 1998, pp. 222-224.
Bohm et al., "The role of sialic acid as a modulator of the anti-inflammatory activity of IgG," Semin Immunopathol. 34(3):443-53 (2012).
Bohne et al., "SWEET—WWW-based rapid 30 construction of oligo- and polysaccharides", Bioinformatics. 15(9): 767-768 (1999).
Bollati-Fogolin et al., "Temperature reduction in cultures of hGM-CSF-expressing CHO cells: effect on productivity and product quality", Biotechnol Prog. 21 (1 ):17-21 (2005).
Bork et al., "Increasing the sialylation of therapeutic glycoproteins: The potential of the sialic acid biosynthetic pathway," J. Pharm. Sci, 2009, 98:3499-3508.
Bowman et al., "Biosynthesis of L-selectin ligands: sulfation of sialyl Lewis x-related oligosaccharides by a family of GlcNAc-6-sulfotransferases", Biochemistry. 40(18):5382-91 (2001).
Breidenbach et al., "Targeted metabolic labeling of yeast N-glycans with unnatural sugars," Proc Natl Acad Sci USA. 107(9):3988-93 (2010).
Broschat et al., "Purification and characterization of GDP-D-mannose 4,6-dehydratase from porcine thyroid", Eur J Biochem. 153(2):397-401 (1985).
Cabrera et al., "Influence of culture conditions on the N-glycosylation of a monoclonal antibody specific for recombinant hepatitis B surface antigen", Biotechnol Appl Biochem. 41(Pt1 ):67-76 (2005).
Campbell et al., "Therapeutic Effect of IVIG on Inflammatory Arthritis in Mice is Dependent on the Fc Portion and Independent of Sialylation or Basophils," J of Immunology., Jun. 1, 2014, 192 (11) 5031-5038.
Candore et al., "Inflammation, Cytokines, Immune Response, Apolipoprotein E, Cholesterol, and Oxidative Stress in Alzheimer Disease: Therapeutic Implications," Rejuvenation Research, 2010, 13(2-3):301-313.
CAS No. 9007-83-4, "γ-Globulins from human blood," retrieved Apr. 5, 2021, retrieved from URL <https://www.sigmaaldrich.com/catalog/product/sigma/g4386?lang=en&region=US>, 3 pages.
Chen & Colley, "Minimal structural and glycosylation requirements for ST6Gal I activity and trafficking" Glycobiology, 2000, 10:531-538.
Chen et al., "Effects of elevated ammonium on glycosylation gene expression in CHO cells", Metab Enq. 8(2):123-32 (2006).
Chen et al., "Independent Lec1A CHO glycosylation mutants arise from point mutations in Nacetylglucosaminyltransferase I that reduce affinity for both substrates. Molecular consequences based on the crystal structure of GlcNAc-TI", Biochemistry. 40(30):8765-72 (2001).
Chen et al., "T cell receptor signaling co-regulates multiple Golgi genes to enhance N-glycan branching," J Biol Chem. 284(47):32454-61 (2009).
Cheng, et al., "Trans-sialidase activity of Photobacterium damsela α2,6-sialyltransferase and its application in the synthesis of sialosides," Glycobiology, 2010, 20:260-268.

(56) References Cited

OTHER PUBLICATIONS

Clark et al., "Gene-expression profiles for five key glycosylation genes for galactose-fed CHO cells expressing recombinant IL-4/13 cytokine trap", Biotechnol Bioeng. 90(5):568-77 (2005).
Communication pursuant to Article 94(3) in European Application No. 13822833.3, dated Aug. 31, 2017, 7 pages.
Communication Pursuant to Article 94(3) in European Application No. 13822833.3, dated Feb. 18, 2021, 4 pages.
Communication Pursuant to Article 94(3) in European Application No. 13822833.3, dated Jan. 21, 2020, 4 pages.
Communication Pursuant to Article 94(3) in European Application No. 13822833.3, dated Nov. 29, 2018, 4 pages.
Communication Pursuant to Article 94(3) in European Application No. 14792116.7, dated Dec. 17, 2018, 5 pages.
Communication pursuant to Article 94(3) in European Application No. 14792116.7, dated Jul. 25, 2017, 6 pages.
Communication Pursuant to Article 94(3) in European Application No. 14792116.7, dated Mar. 12, 2018, 5 pages.
Communication Pursuant to Article 94(3) in European Application No. 14853244.3, dated Jan. 14, 2021, 5 pages.
Communication Pursuant to Article 94(3) in European Application No. 14853244.3, dated Jul. 19, 2019, 7 pages.
Cooper et al., "GlycoSuiteDB: a curated relational database of glycoprotein glycan structures and their biological sources. 2003 update", Nucleic Acids Res. 31 (1):511-3 (2003).
Cooper et al., "GlycoSuiteDB: a new curated relational database of glycoprotein glycan structures and their biological sources," Nucleic Acids Res. 29(1):332-5 (2001).
Cox et al., "Glycan optimization of a human monoclonal antibody in the aquatic plant Lemna minor", Nat Biotechnol. 24(12):1591-7 (2006).
Crowell et al., "Amino acid and manganese supplementation modulates the glycosylation state of erythropoietin in a CHO culture system", Biotechnol Bioeng. 96(3):538-549 (2007) (29 pages).
Cummings et al., "Antibodies and Lectins in Glycan Analysis." Essentials of Glycobiology. Varki A, Cumminas RD, Eska JD et al., 1-17 (2009).
Czajkowsky et al., "Fc-fusion proteins: new developments and future perspectives," EMBO Mol. Med, 2012, 4:1015-1028.
Dalakas, Marinos C. "Subcutaneous IgG for chronic inflammatory demyelinating polyneuropathy." The Lancet. Neurology vol. 17,1 (2018): 20-21. doi:10.1016/S1474-4422(17)30379-4.
Debray et al., Glycoprotein Analysis: General Methods. Encyclopedia of Analytical Chemistry. John Wiley & Sons, 1-39 (2006).
Donadio et al., Recognition of cell surface acceptors by two human a-2,6-sialyltransferases producted in CHO cells. Biochemie, 85:311-321. (2003).
Donaldson et al., "The use of lectins to select subpopulations of insect cells", Biotechnol Bioeng. 64(5):616-9 (1999).
Dorka, Penny, Thesis: "Modelling Batch and Fed-Batch Mammalian Cell Cultures for Optimizing MAb Productivity," Master of Science, University of Waterloo, 2007 (197 pages).
Drecktrah et al., "Inhibition of a Golgi complex lysophospholipid acyltransferase induces membrane tubule formation and retrograde trafficking," Mal Biol Cell. 14(8):3459-69 (2003).
Durandy et al. "Immunoglobulin replacement therapy in primary antibody deficiency 1-16, 19-48, 51-53 diseases—maximizing success," Int Arch Allergy Immunol., Feb. 15, 2005, 136(3):217-229.
Dwyer, "Manipulating the immune system with immune globulin," N Engl J Med. 326(2):107-16 (1992).
Elovaara I. et al., "EFNS guidelines for the use of intravenous immunoglobulin in treatment of neurological diseases," Eur. J. Neur. 2008, 15(9):893-908.
Engel et al., "Rec. ST6Gal-I variants to control enzymatic activity in processes of in vitro glycoengineering," BMC Proceedings, (Suppl 6):P110 (2013).
Extended European Search Report for European Application No. 13822833.3, dated Jun. 6, 2016 (9 pages).
Extended European Search Report for European Application No. 14792116.7, dated Oct. 21, 2016 (9 pages).
Extended European Search Report for European Application No. 14798473.6, dated Oct. 13, 2016 (10 pages).
Extended European Search Report for European Application No. 14853244.3, dated Jun. 8, 2017 (11 pages).
Extended European Search Report for European Application No. 20158041.2, dated Sep. 9, 2020 (9 pages).
Fareed, "S-9-10 synthetic and biotechnology derived glycomimetics. Impact on drug development", Abstract of 6th Proteoglycan Forum, Jun. 24, Hamamatsu, Japan (2000) (1 page).
Feasby et al., "Guidelines on the use of intravenous immune globulin for neurologic conditions," Transfus Med Rev. 21 (2 Suppl 1):S57-107 (2007).
Ferrara et al., "Modulation of therapeutic antibody effector functions by glycosylation engineering: influence of golgi enzyme localization domain and co-expression of heterologous beta1, 4-N-acetylglucosaminyltransferase III and golgi alpha-mannosidase II," Biotechnol Bioeng., 93(5):851-861 (2006).
Fitz et al., "Combined use of subtilisin and N-acetylneuraminic acid aldolase for the synthesis of a fluorescent sialic acid," J Org Chem. 59(26):8279-80 (1994).
Fleischer, "Mechanism of glycosylation in the Golgi apparatus," J Histochem Cytochem. 31 (8):1033-40 (1983).
Forno et al., "N- and O-linked carbohydrates and glycosylation site occupancy in combinant human granulocyte-macrophage colony-stimulating factor secreted by a Chinese hamster ovary cell line," Eur J Biochem. 271 (5):907-19 (2004).
Fukuda et al., "Survival of recombinant erythropoietin in the circulation: the role of carbohydrates", Blood. 73(1):84-89 (1989).
Gajdos et al., "Intravenous Immunoglobulin for myasthenia gravis," Cochrane Database of Systematic Reviews, 2012, 12:1-30.
Gates et al., "Glycobiology Analysis Manual," <http://www.sigmaaldrich.com/lifescience/proteomics/post-translational-analysis/glycosylation/glycoprotein-analysis-manual.html>. retrieved on Nov. 23, 2016 (132 pages).
Gawlitzek et al., "Ammonium alters N-glycan structures of recombinant TNFR-IgG: degradative versus biosynthetic mechanisms", Biotechnol Bioeng. 68(6):637-46 (2000).
Gawlitzek et al., "Characterization of changes in the glycosylation pattern of recombinant proteins from BHK-21 cells due to different culture conditions", J Biotechnol. 42(2):117-131 (1995).
Goldman et al., "Monitoring recombinant human interferon-gamma N-glycosylation during perfused fluidized-bed and stirred-tank batch culture of CHO cells", Biotechnol Bioeng. 60(5):596-607 (1998).
Greer, "Biosimilar developers face a reference-product dilemma," <http://license.icopyright.net/user/viewFreeUse.act?fuid=MTYwMTgONDk%3D>, retrieved on Apr. 9, 2012 (3 pages).
Gu et al., "Improvement of interferon-gamma sialylation in Chinese hamster ovary cell culture by feeding of N-acetylmannosamine", Biotechnol Bioeng. 58(6):642-48 (1998).
Guhr et al., "Enrichment of Sialylated IgG by Lectin Fractionation Does not Enhance the Efficacy of Immunoglobulin G in a Murine Model of Immune Thrombocytopenia," PLOS ONE., Jun. 2011, 6(6):e21246.
Gürcan, Hakan M, and A Razzaque Ahmed. "Efficacy of various intravenous immunoglobulin therapy protocols in autoimmune and chronic inflammatory disorders." The Annals of pharmacotherapy vol. 41,5 (2007): 812-23. doi:10.1345/aph.1K037.
Hahn et al., "Intravenous immunoglobulin treatment in chronic inflammatory demyelinating polyneuropathy: A double-blind, placebo-controlled, cross-over study," Brain, Aug. 1996, 119:1067-1077.
Hara et al., "Determination of mono-O-acetylated N-acetylneuraminic acids in human and rat sera by fluorometric high-performance liquid chromatography," Anal Biochem. 179(1):162-6 (1989).
Hendrick et al., "Increased productivity of recombinant tissular plasminogen activator (t-PA) by butyrate and shift of temperature: a cell cycle phases analysis", Cytotechnology. 36(1-3):71-83 (2001).
Hewitt et al., "Solution and solid-support synthesis of a potential leishmaniasis carbohydrate vaccine", J Org Chem. 66(12):4233-43 (2001).
Hills et al., "Metabolic control of recombinant monoclonal antibody N-glycosylation in GS-Nso cells," Biotechnol Bioenq. 75(2):239-51 (2001).

(56) References Cited

OTHER PUBLICATIONS

Hincal, "An introduction to safety issues in biosimilars/follow-on biopharmaceuticals," J Med CBR Def. 7 (2009) (18 pages).
Hirabayashi et al., "Separation technologies for glycomics", J Chromatog B Analyst Technol Biomed Life Sci. 771 (1-2):67-87 (2002) (Abstract Only) (2 pages).
Hoja-Lukowicz et al., "High-mannose-type oligosaccharides from human placental arylsulfatase A are core fucosylated as confirmed by MALDI MS", Glycobiology. 10(6):551-7(2000).
Hosoi et al., "Modulation of oligosaccharide structure of a pro-urokinase derivative (pro-UK delta GS1) by changing culture conditions of a lymphoblastoid cell line Namalwa KJM-1 adapted to serum-free medium," Cytotechnology. 19(2):125-35 (1996).
Hossler et al., "Systems analysis of N-glycan processing in mammalian cells," PLoS One. 2(8):e713 (2007) (17 pages).
Huang et al., "Chemoenzymatic Glycoengineering of intact IgG Antibodies for Gain of Functions," Journal of the American Chemical Society, Jul. 16, 2012, 134(29):12308-12318.
Iijima (2018); Clin. Expt. Neuroimmunol. 9(2):101-109.
Imai-Nishiya et al., "Double knockdown of alpha1 ,6-fucosyltransferase (FUT8) and GDPmannose 4,6-dehydratase (GMO) in antibody-producing cells: a new strategy for generating fully non-fucosylated therapeutic antibodies with enhanced ADCC", BMC Biotechnol. 7:84 (2007) (13 Pages).
International Preliminary Report on Patentability for International Application No. PCT/IB2021/057659, dated Mar. 2, 2023 (8 pages).
International Preliminary Report on Patentability for International Application No. PCT/US2014/036413, dated Nov. 3, 2015 (25 pages).
International Preliminary Report on Patentability for International Application No. PCT/US2014/037761, dated Nov. 17, 2015 (8 pages).
International Preliminary Report on Patentability for International Application No. PCT/US2014/060363, dated Apr. 19, 2016 (6 pages).
International Preliminary Report on Patentability for International Application No. PCT/US2019/055983, dated Apr. 22, 2021, 13 pages.
International Search Report and Written Opinion for International Application No. PCT/IB2021/057659, dated Feb. 24, 2022 (11 pages).
International Search Report and Written Opinion for International Application No. PCT/US2013/043786, dated Jul. 3, 2014 (21 pages).
International Search Report and Written Opinion for International Application No. PCT/US2013/052040, dated Dec. 3, 2013 (23 pages).
International Search Report and Written Opinion for International Application No. PCT/US2014/036413, dated Nov. 21, 2014 (21 pages).
International Search Report and Written Opinion for International Application No. PCT/US2014/037761, dated Oct. 10, 2014 (11 pages).
International Search Report and Written Opinion for International Application No. PCT/US2014/060363, dated Feb. 4, 2015 (9 pages).
International Search Report and Written Opinion for International Application No. PCT/US2019/055983, dated Jan. 10, 2020, 16 pages.
International Search Report and Written Opinion for International Application No. PCT/US2019/055987, dated Feburary 20, 2020, 14 pages.
Ito et al., Highly Oriented Recombinant Glycosyltransferases: Site-Specific Immobilization of Unstable Membrane Proteins by Using *Staphylococcus aureus* Sortase A. Biochem., 2010, vol. 49: 2604-2614. (2010).
Jabs et al., "Fast and Extensive Mass Spectrometry Characterization of Theraputic mAbs: The Panitumumab Case Study," CASSS Mass Spec Meeting, Poster 125 (2012) (1 page).
Jefferis et al., "IgG-Fc-mediated effector functions: molecular definition of interaction sites for effector ligands and the role of glycosylation," Immunol. Rev., 1998, 163:59-76.
Jefferis, "Glycosylation as a strategy to improve antibody-based therapeutics," Nature Reviews, 2009, 8:226-234.
Joosten et al., "Effect of culture conditions on the degree of sialylation of a recombinant glycoprotein expressed in insect cells", Biotechnol Proq. 19(3):739-49 (2003).
Joziasse et al., "Branch specificity of bovine colostrum CMP-sialic acid: Gal beta 1 4GIcNAc-R alpha 2 6-sialyltransferase. Sialylation of bi-, tri-, and tetraantennary oligosaccharides and qlycopeptides of the N-acetyllactosamine type," J Biol Chem. 262(5):2025-33 (1987).
Kakehi et al., "Analysis of glycoproteins, glycopeptides and glycoprotein-derived oligosaccharides by high-performance capillary electrophoresis," J Chromatogr. 720(1-2):377-93 (1996).
Kalodiki et al., "New and generic anticoagulants and biosimilars: safety considerations," Clin Appl Thromb Hemost. 17(2):136-9 (2011) (5 pages).
Kanda et al., "Comparison of biological activity among nonfucosylated therapeutic IgG1 antibodies with three different N-linked Fe oligosaccharides: the high-mannose, hybrid, and complex types," Glycobiology. 17(1):104-18 (2006).
Kanda et al., "Establishment of a GDP-mannose 4,6-dehydratase (GMO) knockout host cell line: A new strategy for generating completely non-fucosylated recombinant therapeutics," Journal of Biotechnol. 130(3):300-10 (2007) (Abstract Only).
Kaneko et al., "Anti-inflammatory activity of immunoglobulin G resulting from Fe sialylation." Science. 313(5787):670-3 (2006).
Kaneko et al., "Pathology and protection in nephrotoxic nephritis is determined by selective engagement of specific Fe receptors." J Exp Med. 203(3):789-97 (2006).
Kasermann et al., "Analysis and Functional Consequences of Increased Fab-Sialylation of Intravenous Immunoglobulin (IVIG) after Lectin Fractionation," PLOS ONE, Jun. 2012, 7(6):e37243 (With Supplemental Material).
Katz et al. "Intravenous Immunoglobulin: Overview, Uses of Intravenous Immunoglobulin", Pharmacology and Monitoring, https://emedicine.medscape.come/article/210367-overview.
Kawashima et al., "Tyrosine kinase activity of epidermal growth factor receptor is regulated by GM3 binding through carbohydrate to carbohydrate interactions," J Biol Chem. 284(10):6147-55 (2009).
Keiser et al., "Direct isolation and sequencing of specific protein-binding glycosaminoglycans," Nat Med. 7(1):123-8 (2001).
Keppler et al., "Biosynthetic modulation of sialic acid-dependent virus-receptor interactions of two primate polyoma viruses," J Biol Chem. 270(3):1308-14 (1995).
Kile et al., "IVIG treatment of mild cognitive impairment due to Alzheimer's disease: a randomised double-blinded exploratory study of the effect on brain atrophy, cognition and conversion to dementia," J Neurol Neurosurg Psychiatry, Sep. 2015, 0: 1-7.
Kim et al., "Production and N-glycan analysis of secreted human erythropoietin glycoprotein in stably transfected *Drosophila* S2 cells," Biotechnol Bioeng. 92(4):452-61 (2005).
Kosa et al., "Modification of cell surfaces by enzymatic introduction of special sialic acid analogues," Biochem Biophys Res Commun. 190(3):914-20 (1993).
Krapp et al., "Structural analysis of human IgG-Fc glycoforms reveals a correlation between glycosylation and structural integrity," J Mol Biol. 325(5):979-89 (2003).
Kunkel et al., "Comparisons of the glycosylation of a monoclonal antibody produced under nominally identical cell culture conditions in two different bioreactors," Biotechnol Prog. 16(3):462-70 (2000).
Kunkel et al., "Dissolved oxygen concentration in serum-free continuous culture affects N-linked glycosylation of a monoclonal antibody," J Biotechnol. 62(1):55-71 (1998).
Kuter et al., "Thrombopoietin and platelet production in chronic immune thrombocytopenia," Hematol Oncol Clin North Am., Dec. 2009, 23(6):1193-1211.
Kuwano et al., Successful Treatment of Dermatomyositis with High-dose Intravenous Immunoglobulin, Acta Dermato-Venereologica, 2006, 86(2):158-159.
Lance et al., "Isolation and characterization of a partial cDNA for a human sialyltransferase." Biochem Biophys Res Commun. 164(1 ):225-32 (1989).

(56) References Cited

OTHER PUBLICATIONS

Lattova et al., "Alterations in glycopeptides associated with herceptin treatment of human breast carcinoma MCF-7 and T-lymphoblastoid cells," Mol Cell Proteomics. 10(9):M111.007765 (2011) (11 pages).
Le Floch et al., "HPCE monitoring of the N-glycosylation pattern and sialylation of murine erythropoietin produced by CHO cells in batch processes," Biotechnol Prog. 20(3):864-71 (2004).
Legaigneur, et al., "Exploring the acceptor substrate recognition of the human beta-Galactoside alpha2,6-Sialytransferase," J. Biol. Chem., 2001, 276:21608-617.
Lifely et al., "Glycosylation and biological activity of CAMPATH-1 H expressed in different cell lines and grown under different culture conditions," Glycobiology. 5(8):813-22 (1995).
Lin et al., "Unusual stereoselectivity in sialic acid aldolase-catalyzed aldol condensations: synthesis of both enantiomers of high-carbon monosaccharides," J Am Chem Soc. 114(26):10138-45 (1992).
Lipscomb et al., "Effect of production method and gene amplification on the glycosylation pattern of a secreted reporter protein in CHO cells," Biotechnol Prog. 21 (1):40-9 (2005).
Live et al., "Conformational influences of glycosylation of a peptide: a possible model for the effect of glycosylation on the rate of protein folding," Proc Natl Acad Sci USA. 93(23):12759-61 (1996).
Lopez-Avalos et al., "The UDPase activity of the Kluyveromyces lactis Golgi GDPase has a role in uridine nucleotide sugar transport into Golgi vesicles," Glycobiology. 11(5):413-22 (2001).
Ma, et al., "Two naturally occuring alpha2,6-Sialyltransferase forms with a single amino acid change in the catalytic domain differ in their catalytic activity and proteolytic processing," J. Biol. Chem., 1997, 272:672-279.
MacMillan et al., "Selective in vitro glycosylation of recombinant proteins: semi-synthesis of novel homogeneous glycoforms of human erythropoietin," Chem Biol. 8(2):133-45 (2001).
Malissard et al., Improving the solubility of the catalytic domain of human b-1, 4-galactosyltransferase1 through rationally designed amino-acid replacements. Eur. J. Biochem., 2001, vol. 268: 4352-4358 (2001).
Mattu et al., "The Glycosylation and Structure of Human Serum IgA1, Fab, and Fc Regions and the Role of N-Glycosylation on Fcα Receptor Interactions," J. Biol. Chem., 1998, 273:2260-2272.
Misra, "Are biosimilars really generics?" Expert Opin Biol Ther. 10(4):489-94 (2010).
Moran et al., "A systematic approach to the validation of process control parameters for monoclonal antibody production in fed-batch culture of a murine myeloma," Biotechnol Bioeng. 69(3):242-55 (2000).
Mueller et al., "Recombinant glycoprotein product quality in proliferation-controlled BHK-21 cells," Biotechnol Bioeng. 65(5):529-36 (1999).
Nairn et al., "Regulation of glycan structures in animal tissues: transcript profiling of glycanrelated genes," J Biol Chem. 283(25):17298-313 (2008).
Nam et al., "The effects of culture conditions on the glycosylation of secreted human placental alkaline phosphatase produced in Chinese hamster ovary cells," Biotechnol Bioeng. 100(6):1178-92 (2008).
Nettleton et al., "Role of Glycosylation Sites in the IgE Fc Molecule," Int. Arch. Allergy Immunol., 1995, 107:328-329.
Nimmerjahn et. al., "The antiinflammatory activity of IgG: the intravenous IgG paradox," J Exp Med. 204(1 ):11-5 (2007).
Nowicki, "Basic facts about biosimilars," Kidney Blood Press Res. 30:267-72 (2007).
Nyberg et al., "Metabolic effects on recombinant interferon-gamma glycosylation in continuous culture of Chinese hamster ovary cells," Biotechnol Bioeng. 62(3):336-47 (1999).
Oh et al., "Effect of N-acetylcystein on butyrate-treated Chinese hamster ovary cells to improve the production of recombinant human interferon-beta-1 a," Biotechnol Prog. 21(4):1154-64 (2005).
Pace et al., "Characterization of minor N-linked glycans on antibodies using endo H release and MALDI-mass spectrometry," Anal Lett. 42:1711-24 (2009).
Park et al., "Expression of carbamoyl phosphate synthetase I and ornithine transcarbamoylase genes in Chinese hamster ovary dhfr-cells decreases accumulation of ammonium ion in culture media," J Biotechnol. 81 (2-3):129-40 (2000).
Parmley, "Sweetening Immunoglobulins," Biocentury Innovations. Bernstein (2015)(2 pages).
Plante et al., "Automated solid-phase synthesis of oligosaccharides," Science. 291 (5508):1523-7 (2001).
Plante et al., "Formation of beta-glucosamine and beta-mannose linkages using glycosyl phosphates," Org Lett. 2(24):3841-3 (2000).
Rader, "Nomenclature of new biosimilars will be highly controversial," BioProcess International. 9:28-32 (2011).
Raju, "Terminal sugars of Fe glycans influence antibody effector functions of IgGs," Curr Opin Immunol. 20(4):471-8 (2008).
Ramakrishna et al., Passively Administered Pooled Human Immunoglobulins Exert IL-10 Dependent Anti-Inflammatory Effects that Protect against Fatal HSV Encephalitis., Jun. 2, 2011, 7(6):1-17.
Raymond et al., Production of Highly Sialylated Monoclonal Antibodies. Biochemistry, Genetics and Molecular Bioloqv-Glvcosvlation. Stefana Petrescu, 397-418 (2012).
Reitman et al., "Mouse lymphoma cell lines resistant to pea lectin are defective in fucose metabolism", J Biol Chem. 255(20):9900-6 (1980).
Restelli et al., "The effect of dissolved oxygen on the production and the glycosylation profile of recombinant human erythropoietin produced from CHO cells", Biotechnol Bioeng. 94(3):481-94 (2006).
Ripka et al., "Two Chinese hamster ovary glycosylation mutants affected in the conversion of GDP-mannose to GDP-fucose," Arch Biochem Biophys. 249(2):533-45 (1986).
Ritzenthaler et al., "Reevaluation of the effects of brefeldin A on plant cells using tobacco Bright Yellow 2 cells expressing Golgi-targeted green fluorescent protein and COPI antisera," Plant Cell. 14(1):237-61 (2002).
Robinson et al., "Characterization of a recombinant antibody produced in the course of a high yield fed batch process," Biotechnol Bioeng. 44(6):727-35 (1994).
Rodriguez et al., "Enhanced production of monomeric interferon-beta by CHO cells through the control of culture conditions," Biotechnol Prog. 21(1):22-30 (2005).
Roger, "Biosimilars: current status and future directions," Expert Opin Biol Ther. 10(7):1011-8 (2010).
Rudiger et al., "Breaking the sugar code: six levels of affinity regulation in glycan-lectin interaction," Crackina the Suaar Code by Naviaatina the Glycospace. Germany, 11-28 (2011 ).
Ruisi et al., "Stability of measurement of the immature platelet fraction," Am J Hematol. 85(8):622-4 (2010).
Santell et al., "Aberrant metabolic sialylation of recombinant proteins expressed in Chinese hamster ovary cells in high productivity cultures," Biochem Biophys Res Commun. 258(1):132-7 (1999).
Sasaki et al., "Site-specific glycosylation of human recombinant erythropoietin: analysis of glycopeptides or peptides at each glycosylation site by fast atom bombardment mass spectrometry," Biochemistry. 27(23):8618-26 (1988).
Sazinsky et al., "Aglycosylated immunoglobulin G1 variants productively engage activating Fc receptors," Proc Natl Acad Sci USA., Dec. 23, 2008, 105(51):20167-20172.
Schellekens and Moore, "Clinical comparability and European biosimilar regulations," Nat Biotechnol, Jan. 2010, 28(1):28-31.
Schellekens, "Biosimilar therapeutics—what do we need to consider?" NDT Plus, 2009, 2(Suppl_ 1):i27-i36.
Schiestl et al., "Acceptable changes in quality attributes of glycosylated biopharmaceuticals." Nat Biotechnol. 29(4):310-2 (2011).
Schulz et al., "Mediators of galactose sensitivity in UDP-galactose 4'-epimerase-impaired mammalian cells," J Biol Chem. 280(14):13493-502 (2005).
Schuster et al., "Improved effector functions of a therapeutic monoclonal Lewis Y-specific antibody by glycoform engineering," Cancer Res. 65(17):7934-41 (2005).

(56) References Cited

OTHER PUBLICATIONS

Schwab et al., "Intravenous immunoglobulin therapy: how does IgG modulate the immune system?," Nat Rev Immunol. 13(3): 176-89 (2013).
Schwab et al., "IVI g-mediated amelioration of ITP in mice is dependent on sialic acid and SIGNR 1," Eur J Immunol., Jan. 26, 2012, 42:826-830.
Sekhon et al., "Biosimilars: an overview," Biosimilars. 2011 (1 ):1-11 (2011).
Senger et al., "Effect of shear stress on intrinsic CHO culture state and glycosylation of recombinant tissue-type plasminogen activator protein," Biotechnol Prog. 19(4):1199-209 (2003).
Serrato et al., "Heterogeneous conditions in dissolved oxygen affect N-glycosylation but not productivity of a monoclonal antibody in hybridoma cultures", Biotechnol Bioeng. 88(2):176-188-2004.
Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology. 1(2):187-191 (1991).
Shang et al., "Development and application of a robust N-glycan profiling method for heightened characterization of monoclonal antibodies and related glycoproteins," J Ph arm Sci. 103(7): 1967-78 (2014).
Sherman, Rachel E., "Biosimilar Biological Products". Biosimilar Guidance Webinar. Food and Drug Administration (2012) (22 pages).
Shinkawa et al., "The absence of fucose but not the presence of galactose or bisecting Nacetylglucosamine of human IgG1 complex-type oligosaccharides shows the critical role of enhancing antibody-dependent cellular cytotoxicity," J Biol Chem. 278(5):3466-73 (2003).
Siberil et al., "Intravenous immunoglobulins in autoimmune and inflammatory diseases: a mechanistic perspective." Ann NY Acad Sci. 1110:497-506 (2007).
Sokolowski et al., "Conformational analysis of biantennary glycans and molecular modeling of their complexes with lentil lectin", J Mal Graph Model. 15(1):37-42 (1997).
Sparks et al., "Synthesis of potential inhibitors of hemagglutination by Influenza virus: chemoenzymic preparation of N-5 analogs of N-acetylneuraminic acid", Tetrahedron. 49(1):1-12 (1993).
Spearman et al., "Production and glycosylation of recombinant beta-interferon in suspension and cytopore microcarrier cultures of CHO cells", Biotechnol Prog. 21 (1):31-9 (2005).
Srinivas et al., "Assessment of dose proportionality, absolute bioavailability, and immunogenicity response of CTLA41g (BMS-188667), a novel immunosuppressive agent, following subcutaneous and intravenous administration to rats," Pharm Res. 14(7) :911-6 (1997).
Srinivas et al., "Pharmacokinetics and pharmacodynamics of CTLA41g (BMS-188667), a novel immunosuooressive agent, in monkeys following multiple doses," J Pharm Sci. 85(1):1-4 (1996).
Stadlmann et al., "Analysis of immunoglobulin glycosylation by LC-ES I-MS of glycopeptides and oliqosaccharides," Proteomics. 8:2858-71 (2008).
Stadlmann et al., "Analytical and Functional Aspects of Antibody Sialylation," J Clin Immunol., May 2010, 30(Suppl 1):S15-S19.
Sticher, et al., "Purification and characterization of alpha(2-6)-sialyltransferase from human liver," Blycoconjugate J., 1991, 8:45-54.
Sung et al., "Effect of sodium butyrate on the production, heterogeneity and biological activity of human thrombopoietin by recombinant Chinese hamster ovary cells," J Biotechnol. 112(3):323-35 (2004).
Takeuchi et al., "Structures and functional roles of the sugar chains of human erythropoietins," Glycobiology. 1(4):337-346 (1991).
Tan et al., "Characterization and comparison of commercially available TNF receptor 2-Fc fusion protein products." Mabs. 4(6):761-74 (2012).
Third-Party Observation pursuant to Rule 114(2) EPC for European Patent Application No. 13796989.5, dated Jun. 22, 2016 (14 pages).
Tran et al., "Separation of carbohydrate-mediated microheterogeneity of recombinant human erythropoietin by free solution capillary electrophoresis. Effects of pH, buffer type and organic additives," J Chromatogr. 542(2):459-71 (1991).
Trombetta et al., "Glycoprotein reglucosylation and nucleotide sugar utilization in the secretory pathway: identification of a nucleoside diphosphatase in the endoplasmic reticulum," EMBO J. 18(12):3282-92 (1999).
Trummer et al., "Process parameter shifting: Part I. Effect of DOT, pH, and temperature on the performance of Epo-Fc expressing CHO cells cultivated in controlled batch bioreactors," Biotechnol Bioeng. 94(6):1033-44 (2006).
Umana et al., "Engineered glycoforms of an antineuroblastoma IgG1 with optimized antibodydependent cellular cytotoxic activity," Nat Biotechnol. 17(2):176-80 (1999).
Van Berkel et al., "N-linked glycosylation is an important parameter for optimal selection of cell lines producing biopharmaceutical human IgG," Biotechnol Prag. 25(1):244-51 (2009).
Van Den Nieuwenhof et al., "Recombinant glycodelin carrying the same type of glycan structures as contraceptive glycodelin-A can be produced in human kidney 293 cells but not in Chinese hamster ovary cells," Eur J Biochem. 267(15):4753-62 (2000).
Varki, "Radioactive tracer techniques in the sequencing of glycoprotein oligosaccharides," FASEB J. 5(2):226-35 (1991).
Vattepu et al. Front Immunol. doi: 10.3389/fimmu.2022.818736, Apr. 7, 2022.
Väzquez-Moreno, L et al. "Hypersialylated macromolecular serum immunoglobulin A1 in type 2 diabetes mellitus." Clinical biochemistry vol. 34,1 (2001): 35-41. doi: 10.1016/s0009-9120(00)00192-2.
Venkataraman et al., "Sequencing complex polysaccharides," Science. 286(5439):537-42 (1999).
Von Der Lieth, "Expanding proteomics to glycobiology: biocomputing approaches understanding the function of sugar," Pacific Symposium on Biocomputing; Kauai, Hawaii (Abstract only) (2 pages) (2002).
Wang et al., "EDEM an ER quality control receptor," Nat Struct Biol. 10(5):319-21 (2003).
Warrington et al., in Naturally Occurring Antibodies (NAbs), edited by Hans U. Lutz, copyright 2012 Landes Bioscience and Springer Science+Business Media.
Washburn, Nathaniel et al. "Controlled tetra-Fc sialylation of IVIg results in a drug candidate with consistent enhanced anti-inflammatory activity." Proceedings of the National Academy of Sciences of the United States of America vol. 112,11 (2015): E1297-306. doi:10.1073/pnas.1422481112.
Watson et al., "Capillary electrophoretic separation of human recombinant erythropoietin (r-HuEPO) glycoforms," Anal Biochem. 210(2):389-93 (1993).
Watson et al., "Structure determination of the intact major sialylated oligosaccharide chains of recombinant human erythropoietin expressed in Chinese hamster ovary cells," Glycobiology. 4(2):227-37 (1994).
Webb et al., "Structural characterization of intact, branched oligosaccharides by high performance liquid chromatography and liquid secondary ion mass spectrometry," Anal Biochem. 169(2):337-49 (1988).
Weikert, S et al. "Engineering Chinese hamster ovary cells to maximize sialic acid content of recombinant glycoproteins." Nature biotechnology vol. 17,11 (1999): 1116-21. doi:10.1038/15104.
Weiner et al., "A sensitive enzyme immunoassay for the quantitation of human CTLA41g fusion protein in mouse serum: pharmacokinetic application to optimizing cell line selection," J Pharm Biomed Anal. 15(5):571-9 (1997).
Wong et al., "Impact of dynamic online fed-batch strategies on metabolism, productivity and Nglycosylation quality in CHO cell cultures," Biotechnol Bioeng. 89(2):164-77 (2005).
Wootla et al., "Polyclonal and monoclonal antibodies in clinic," Methods Mol Biol., Sep. 2013, (1060):79-110.
Wopereis et al., "Mechanisms in protein O-glycan biosynthesis and clinical and molecular aspects of protein O-glycan biosynthesis defects: a review," Clin Chem. 52(4):574-600 (2006).
Wormald et al., "Variations in oligosaccharide-protein interactions in immunoglobulin G determine the site-specific glycosylation

(56) References Cited

OTHER PUBLICATIONS profiles and modulate the dynamic motion of the Fc oligosaccharides," Biochemistry, 1997, 36(6):1370-1380.
Wright et al., "Effect of glycosylation on antibody function: implications for genetic engineering," Trends Biotech, 1997, 15:26-32.
Wright et al., "In vivo trafficking and catabolismof IgG1 antibodies with Fe associated carbohydrates of differing structure," Glycobiology. 10(12):1347-55 (2000).
Yang et al., "Achievement of high cell density and high antibody productivity by a controlled-fed perfusion bioreactor process," Biotechnol Bioeng. 69(1):74-82 (2000).
Yang et al., "Bio-basis function neural network for prediction of protease cleavage sites in proteins," IEEE Trans Neural Netw. 16(1):263-74 (2005).
Yang et al., "Effect of ammonia on the glycosylation of human recombinant erythropoietin in culture," Biotechnol Prog. 16(5):751-9 (2000).
Ye et al., "N-glycan branching requirement in neuronal and postnatal viability," Glycobiology. 14(6):547-58 (2004).
Yoon et al., "Effect of culture pH on erythropoietin production by Chinese hamster ovary cells grown in suspension at 32.5 and 37.0 degrees C," Biotechnol Bioeng. 89(3):345-56 (2005).
Yoon et al., "Effect of simultaneous application of stressful culture conditions on specific productivity and heterogeneity of erythropoietin in Chinese hamster ovary cells," Biotechnol Prog. 20(4):1293-6 (2004).
Yuen et al., "Relationships between the N-glycan structures and biological activities of recombinant human erythropoietins produced using different culture conditions and purification procedures," Br J Haematol. 121 (3):511-26 (2003).
Yuk et al., "Changes in the overall extent of protein glycosylation by Chinese hamster ovary cells over the course of batch culture", Biotechnol Appl Biochem. 36(Pt 2):133-40 (2002).
Yuk et al., "Glycosylation by Chinese hamster ovary cells in dolichol phosphate-supplemented cultures," Biotechnol Appl Biochem. 36(Pt 2):141-7 (2002).
Zhang et al. "Sialylated intravenous immunoglobulin suppress anti-ganglioside antibody mediated nerve injury," Exp Neurol., May 18, 2016, 282:49-55.
Zhang et al., "Glycoengineered Pichia produced anti-HER2 is comparable to trastuzumab in preclinical study." MAbs. 3(3): 289-98 (2011).
Zhang et al., "Quantitative analysis and process monitoring of site-specific glycosylation microheterogeneity in recombinant human interferon-gamma from Chinese hamster ovary cell culture by hydrophilic interaction chromatography," J Chromatogr B Bio med Sci Appl. 712(1-2):73-82 (1998).
U.S. App. No. 17/284,188, filed Apr. 9, 2021.
U.S. App. No. 14/416,869, filed Jan. 23, 2015.
U.S. App. No. 15/957,703, filed Apr. 19, 2018.
U.S. App. No. 17/508,026, filed Oct. 22, 2021.
U.S. App. No. 14/787,403, filed Oct. 27, 2015.
U.S. App. No. 15/954,146, filed Apr. 16, 2018.
U.S. App. No. 16/589,634, filed Oct. 1, 2019.
U.S. App. No. 17/033,452, filed Sep. 25, 2020.
U.S. App. No. 17/032,994, filed Sep. 25, 2020.
U.S. App. No. 17/100,428, filed Nov. 20, 2020.
U.S. App. No. 18/217,401, filed Jun. 30, 2023.
U.S. App. No. 18/218,535, filed Jul. 5, 2023.
U.S. App. No. 18/218,996, filed Jul. 6, 2023.
U.S. App. No. 15/028,917, filed Apr. 12, 2016.
U.S. App. No. 15/985,288, filed May 21, 2018.
U.S. App. No. 16/688,772, filed Nov. 19, 2019.
U.S. App. No. 18/136,803, filed Apr. 19, 2023.
U.S. App. No. 14/890,865, filed Nov. 12, 2015.
U.S. App. No. 16/671,595, filed Nov. 1, 2019.
U.S. App. No. 17/739,912, filed May 9, 2022.
U.S. App. No. 17/602,156, filed Oct. 7, 2021.
U.S. App. No. 17/925,999, filed Nov. 17, 2022.
U.S. App. No. 17/802,441, filed Aug. 25, 2022.
U.S. App. No. 17/926,102, filed Nov. 17, 2022.
U.S. App. No. 17/909,282, filed Sep. 2, 2022.
U.S. App. No. 18/022,069, filed Feb. 17, 2023.
U.S. App. No. 18/022,061, filed Feb. 17, 2023.
U.S. App. No. 18/037,378, filed May 17, 2023.
Andreescu, S. et al., "Affinity immobilization of tagged enzymes." En J. M. Guisan (Ed.) Immobilization of enzymes and cells (2nd ed., pp. 97-106). Totowa, NJ: Humana Press. (2006).
Borek, "Deletion of Genes Encoding Arginase Improves use of 'Heavy' Isotope-Labeled Arginine for Mass Spectrometry in Fission Yeast" PLoS ONE 10(6) 2015: e0129548. (2015).
Gaberc-Porekar, V. et al. "Perspectives of immobilized-metal affinity chromatography". Journal of biochemical and biophysical methods, 49(1-3), 335-360. https://doi.org/10.1016/s0165-022x(01)00207-x.
Guo et al., "More comprehensive standards for monitoring glycosylation" Analytical Biochemistry vol. 612 Aug. 1, 2020, 113896 (2020).
Mestrom, L., et al. "Leloir Glycosyltransferases in Applied Biocatalysis: A Multidisciplinary Approach." International Journal of Molecular Sciences, 20(21), 5263. https://doi.org/10.3390.ijms20215263.
Morrison et al., Studies on galactosyltransferase. Kinetic investigations with N-acertylglucosamine as the galactosyl group acceptor. Journal of Biological Chemistry. 1971. v.246, n.12, p. 3977-3984.
Tayi, V. S. et al., Solid-Phase Enzymatic Remodeling Produces High Yields of Single Glycoform Antibodies. Biotechnology Journal, 13(4), e1700381. https://doi.org/10.1002/biot.201700381.
Veillon et al., "Characterization of isomeric glycan structures by LC-MS/MS", Electrophoresis 2017, 38, 2100-2114 (2017).
Zhao et al., "One-step immobilization and purification of genetic engineering CBD fusion EndoS on cellulose for antibodies Fc-glycan remodeling", Bioorganic Chemistry vol. 91, 8 pgs, (2019).
Zucca et al., "Agarose and its Derivatives as Supports for Enzyme Immobilization". Molecules, 25 pgs, (2016).
Jeanneau et al., "Structure-Function Analysis of the Human Sialyltransferase ST3Gal I: Role of N-Glycosylation and a Novel Conserved Sialylmotif", 2004, Journal of Biological Chemistry, 279(14); 13461-13468.
Moh, S., "Platforms for In Vitro Glycoengineering of proteins." PhD. Thesis, Macquarie Univ., Australia, 2018, pp. 1-165.
Teska, Brandon M et al. "Aggregation and Particle Formation of Therapeutic Proteins in Contact With a Novel Fluoropolymer Surface Versus Siliconized Surfaces: Effects of Agitation in Vials and in Prefilled Syringes." Journal of pharmaceutical sciences vol. 105,7 (2016): 2053-65.

* cited by examiner

A. SEQ ID NO:1

MTRLTVLALLAGLLASSRAGSSPLLAMEWSHPQFEKLEGGGSGGGSGGSWSHPQFEKH
AHAHSRKDHLIHNVHKEEHAHAHNKELGTAVFQGPMRRAIRGRSFQVWNKDSSSKNLIP
RLQKIWKNYLSMNKYKVSYKGPGPGIKFSAEALRCHLRDHVNVSMVEVTDFPFNTSEWE
GYLPKESIRTKAGPWGRCAVVSSAGSLKSSQLGREIDDHDAVLRFNGAPTANFQQDVGT
KTTIRLMNSQLVTTEKRFLKDSLYNEGILIVWDPSVYHSDIPKWYQNPDYNFFNNYKTYRK
LHPNQPFYILKPQMPWELWDILQEISPEEIQPNPPSSGMLGIIIMMTLCDQVDIYEFLPSKR
KTDVCYYYQKFFDSACTMGAYHPLLYEKNLVKHLNQGTDEDIYLLGKATLPGFRTIHCPG

FIG. 3A

B. SEQ ID NO:2

GSYYDSFKLQTKEFQVLKSLGKLAMGSDSQSVSSSSTQDPHRGRQTLGSLRGLAKAKPE
ASFQVWNKDSSSKNLIPRLQKIWKNYLSMNKYKVSYKGPGPGIKFSAEALRCHLRDHVNV
SMVEVTDFPFNTSEWEGYLPKESIRTKAGPWGRCAVVSSAGSLKSSQLGREIDDHDAVL
RFNGAPTANFQQDVGTKTTIRLMNSQLVTTEKRFLKDSLYNEGILIVWDPSVYHSDIPKWY
QNPDYNFFNNYKTYRKLHPNQPFYILKPQMPWELWDILQEISPEEIQPNPPSSGMLGIIIM
MTLCDQVDIYEFLPSKRKTDVCYYYQKFFDSACTMGAYHPLLYEKNLVKHLNQGTDEDIY
LLGKATLPGFRTIHC

FIG. 3B

C. SEQ ID NO:3

MIHTNLKKKFSYFILAFLLFALICVWKKGSYEALKLQAKEFQVTKSLEKLAIGSGSQSTSASI
KQDSKPGSQVLSHLRVTAKVKPQSPYQVWDKNSSSKNLNPRLQKILKNYLSMNKYKVSY
KGPGPGVKFSVEALRCHLRDRVNVSMIEATDFPFNTTEWEGYLPKENFRTKAGPWHRC
AVVSSAGSLKSSHLGKEIDSHDAVLRFNGAPVADFQQDVGMKTTIRLMNSQLITTEKQFL
KDSLYNEGILIVWDPSLYHADIPNWYKKPDYNFFETYKSYRKLYPSQPFYILRPQMPWEL
WDIIQEIAPDRIQPNPPSSGMLGIIIMMTLCDQVDVYEFLPSKRKTDVCYYHQKFFDSACT
MGAYHPLLFEKNMVKQLNEGTDEDIYIFGKATLSGFRTIHC

FIG. 3C

SIALYLATED GLYCOPROTEINS

CROSS REFERENCE TO RELATED APPLICATIONS

This application is a divisional of U.S. patent application Ser. No. 15/985,288, filed on May 21, 2018, now U.S. Pat. No. 11,661,456, which is a continuation of U.S. patent application Ser. No. 15/028,917, filed on Apr. 12, 2016 (now abandoned), which is national stage application under 35 U.S.C. § 371 of International Application Number PCT/US2014/060363, filed on Oct. 14, 2014, which claims the benefit of U.S. Provisional Application No. 61/891,778, filed Oct. 16, 2013, which are hereby incorporated by reference in their entirety.

SEQUENCE LISTING

This application contains a Sequence Listing that has been submitted electronically as an XML file named "14131-0144004_SL_ST26.XML." The XML file, created on Apr. 20, 2023, is 4,779 bytes in size. The material in the XML file is hereby incorporated by reference in its entirety.

BACKGROUND

Therapeutic glycoproteins are an important class of therapeutic biotechnology products, and therapeutic Fc containing glycoproteins, such as IVIg, Fc-receptor fusions, and antibodies (including murine, chimeric, humanized, and human antibodies and fragments thereof) account for the majority of therapeutic biologic products.

SUMMARY OF THE INVENTION

The invention encompasses, in part, the discovery that Fc-containing polypeptides that include branched glycans and that are di-sialylated on the branched glycan (e.g., on an α 1,3 and/or α 1,6 arm in the Fc region's N-linked glycosylation site), with, e.g., a NeuAc-α 2,6-Gal terminal linkage, exhibit improved biological activity, e.g., relative to a reference glycoprotein, e.g., in the treatment of hematological disease, e.g., immune-related thrombocytopenia (ITP). The present disclosure provides, in part, methods for treating hematological disease, e.g., immune-related thrombocytopenia and related diseases by administering compositions containing such Fc-containing polypeptides as well as methods for evaluating, identifying, and/or producing (e.g., manufacturing) such polypeptides.

In one aspect, the invention features a pharmaceutical preparation formulated for subcutaneous administration (e.g., at a concentration of 50-250 mg/mL, e.g., 50-100 mg/mL, 75-125 mg/mL, 100-150 mg/mL, 125-175 mg/mL, 150-200 mg/mL, 175-225 mg/mL, 200-250 mg/mL). This preparation includes polypeptides having an Fc region, wherein at least 50% (e.g., 60%, 70%, 80%, 82%, 85%, 87%, 90%, 92%, 94%, 95%, 97%, 98% up to and including 100%) of branched glycans on the Fc region are di-sialylated by way of NeuAc-α 2,6-Gal terminal linkages. In some embodiments, less than 50% (e.g., less than 40%, 30%, 20%, 15%, 10%, 5%, 4%, 3%, 2%, 1%) of branched glycans on the Fc region are mono-sialylated (e.g., on the α 1,3 arm or the α 1,6 arm) by way of a NeuAc-α 2,6-Gal terminal linkage.

In another aspect, the invention features a pharmaceutical preparation including polypeptides having an Fc region, wherein at least 50% (e.g., 60%, 70%, 80%, 82%, 85%, 87%, 90%, 92%, 94%, 95%, 97%, 98% up to and including 100%) of branched glycans on the Fc region are di-sialylated by way of NeuAc-α 2,6-Gal terminal linkages and less than 50% (e.g., less than 40%, 30%, 20%, 10%, 15%, 5%, 4%, 3%, 2%, 1%) of branched glycans on the Fc region are mono-sialylated on the α 1,3 arm by way of a NeuAc-α 2,6-Gal terminal linkage.

In another aspect, the invention features a pharmaceutical preparation comprising polypeptides having an Fc region, wherein at least 50% (e.g., 60%, 70%, 80%, 82%, 85%, 87%, 90%, 92%, 94%, 95%, 97%, 98% up to and including 100%) of branched glycans on the Fc region are di-sialylated by way of NeuAc-α 2,6-Gal terminal linkages and less than 50% (e.g., less than 40%, 30%, 20%, 10%, 5%, 4%, 3%, 2%, 1%) of branched glycans on the Fc region are mono-sialylated on the a 1,6 arm by way of a NeuAc-α 2,6-Gal terminal linkage.

In another aspect, the invention features a pharmaceutical preparation comprising polypeptides having an Fc region, wherein at least 85% of branched glycans on the Fc region are di-sialylated by way of NeuAc-α 2,6-Gal terminal linkages.

In some embodiments of any of the foregoing preparations, the polypeptides consist essentially of an Fc region. In other embodiments of any of the foregoing preparations, the polypeptides further include a Fab region, a heterologous polypeptide sequence such as a biological receptor sequence (e.g., the polypeptides are Fc-receptor fusion proteins), or a heterologous non-polypeptide moiety.

In certain embodiments, at least 10% (e.g., 20%, 30%, 40%, 50%, 60% 70% or more) of branched glycans on the Fab region or heterologous polypeptide sequence of the polypeptides are mono-sialylated or di-sialylated. In other embodiments, less than 80% (e.g., 70%, 60, 50%, 40%, 30%, 20%, 10%, 5% or less) of branched glycans on the Fab region or heterologous polypeptide sequence of the polypeptides are mono-sialylated or di-sialylated.

In some embodiments of any of the foregoing preparations, the polypeptides are recombinant polypeptides. In other embodiments of any of the foregoing preparations, the polypeptides are derived from plasma, e.g., human plasma. In certain embodiments, the polypeptides are IgG polypeptides (e.g., IgG1, IgG2, IgG3 or IgG4) or the polypeptides consist essentially of an Fc region derived from IgG polypeptides.

In another aspect, the invention features a method of increasing reticulated platelets in a subject in need thereof, comprising administering to the subject any one of the foregoing preparations.

In another aspect, the invention features a method of producing new platelets in a subject in need thereof, comprising administering to the subject any one of the foregoing preparations.

In another aspect, the invention features a method of increasing reticulated platelets or producing new platelets in a subject in need thereof, comprising administering to the subject a pharmaceutical preparation comprising polypeptides comprising an Fc region, wherein at least 85% of branched glycans on the Fc region are di-sialylated by way of NeuAc-α 2,6-Gal terminal linkages.

In some embodiments of any of the foregoing methods, the subject is not being treated with thrombopoietin or a thrombopoietin receptor agonist (e.g., romiplostim, eltrombopag). In some embodiments of any of the foregoing methods, the subject has failed treatment with thrombopoietin or a thrombopoietin receptor agonist (e.g., romiplostim, eltrombopag). In other embodiments of any of the foregoing methods, the subject has a hematological disease such as immune-related thrombocytopenia. In certain embodiments of any of the foregoing methods, the method further includes, after the administering step, the step of determining the total platelet count and/or the reticulated platelet count in the subject, e.g., wherein the total platelet count and/or the reticulated platelet count increases as a result of the administering step. In some embodiments, the method further includes after the determining step, the step of adjusting the dose of the administered pharmaceutical preparation.

DESCRIPTION OF THE FIGURES

FIG. 3A depicts an exemplary ST6 sialyltransferase amino acid sequence (SEQ ID NO:1). FIG. 3B depicts an exemplary ST6 sialyltransferase amino acid sequence (SEQ ID NO:2). FIG. 3C depicts an exemplary ST6 sialyltransferase amino acid sequence (SEQ ID NO:3).

DETAILED DESCRIPTION OF THE INVENTION

Figure 1:
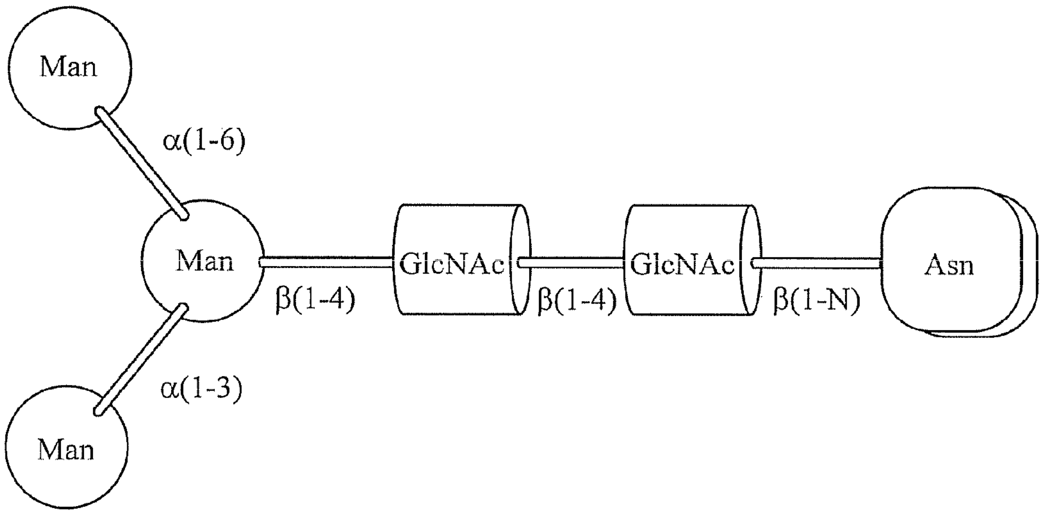
FIG. 1 is a schematic illustration of a common core pentasaccharide $(Man)_3(GlcNAc)(GlcNAc)$ of N-glycans.

Antibodies are glycosylated at conserved positions in the constant regions of their heavy chain. For example, IgG antibodies have a single N-linked glycosylation site at Asn297 of the CH2 domain. Each antibody isotype has a distinct variety of N-linked carbohydrate structures in the constant regions. For human IgG, the core oligosaccharide normally consists of $GlcNAc_2Man_3GlcNAc$, with differing numbers of outer residues. Variation among individual IgG's can occur via attachment of galactose and/or galactose-sialic acid at one or both terminal GlcNAc or via attachment of a third GlcNAc arm (bisecting GlcNAc).

The present disclosure encompasses, in part, pharmaceutical preparations including polypeptides having an Fc region having particular levels of branched glycans that are sialylated on both of the branched glycans in the Fc region (e.g., with a NeuAc-$\alpha$ 2,6-Gal terminal linkage). The levels can be measured on an individual Fc region (e.g., the number of branched glycans that are sialylated on an $\alpha$1,3 arm, an $\alpha$1,6 arm, or both, of the branched glycans in the Fc region), or on the overall composition of a preparation of polypeptides (e.g., the number or percentage of branched glycans that are sialylated on an $\alpha$1,3 arm, an $\alpha$1,6 arm, or both, of the branched glycans in the Fc region in a preparation of polypeptides).

The inventors have discovered that Fc-region containing polypeptides having branched glycans that are preferentially di-sialylated (e.g., with NeuAc-$\alpha$ 2,6-Gal terminal linkages) exhibit improved biological activity, e.g., relative to a reference glycoprotein, and are useful in the treatment of immune-related thrombocytopenia and related diseases.

Preparations useful herein can be obtained from any source. In some instances, providing or obtaining a preparation (e.g., such as a biologic drug substance or a precursor thereof), e.g., that is or includes a polypeptide, can include providing a host cell, e.g., a mammalian host cell (e.g., a CHO cell) that is genetically engineered to express a polypeptide (e.g., a genetically engineered cell); culturing the host cell under conditions suitable to express the polypeptide (e.g., mRNA and/or protein); and, optionally, purifying the expressed polypeptide, e.g., in the form of a recombinant fusion protein) from the cultured cell, thereby producing a preparation.

Definitions

As used herein, "acquire or acquiring (e.g., acquiring information)" means obtaining possession of a physical entity, or a value, e.g., a numerical value, by "directly acquiring" or "indirectly acquiring" the physical entity or value. "Directly acquiring" means performing a process (e.g., performing an assay or test on a sample or "analyzing a sample" as that term is defined herein) to obtain the physical entity or value. "Indirectly acquiring" refers to receiving the physical entity or value from another party or source (e.g., a third party laboratory that directly acquired the physical entity or value). "Directly acquiring" a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Directly acquiring" a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are shown in Table 1.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions. The term "antibody" encompasses antigen-binding fragments of antibodies (e.g., single chain antibodies, Fab, $F(ab')_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

As used herein, a "batch" of a preparation refers to a single production run. Evaluation of different batches thus means evaluation of different production runs or batches. As used herein "sample(s)" refer to separately procured samples. For example, evaluation of separate samples could mean evaluation of different containers or vials of the same batch or from different batches. A batch can include a drug substance batch or a drug product batch.

As used herein, the term "constant region" refers to a polypeptide that corresponds to, or is derived from, one or more constant region immunoglobulin domains of an antibody. A constant region can include any or all of the following immunoglobulin domains: a $C_H1$ domain, a hinge region, a $C_H2$ domain, a $C_H3$ domain (derived from an IgA, IgD, IgG, IgE, or IgM), and a $C_H4$ domain (derived from an IgE or IgM).

As used herein, "evaluating," e.g., in the evaluation/evaluating, identifying, and/or producing aspects disclosed herein, means reviewing, considering, determining, assessing, analyzing, measuring, and/or detecting the presence, absence, level, and/or ratio of one or more parameters in a preparation to provide information pertaining to the one or more parameters. In some instances, evaluating can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. "Evaluating" can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

As used herein, the term "Fc region" refers to a dimer of two "Fc polypeptides," each "Fc polypeptide" including the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or the entire flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cal) and Cα2. An Fc region can be synthetic, recombinant, or generated from natural sources such as IVIg.

An "Fc region-containing polypeptide" is a polypeptide that includes all or a substantial portion of an Fc region. Examples of an Fc region-containing polypeptide preparation include, e.g., a preparation of Fc fragments, a preparation of antibody molecules, a preparation of Fc-fusion proteins (e.g., an Fc-receptor fusion protein), and a preparation of pooled, polyvalent immunoglobulin molecules (e.g., IVIg). Such an Fc region-containing polypeptide may be recombinant (e.g., a recombinant Fc fragment preparation or a recombinant antibody preparation) or naturally derived (such as IVIg).

As used herein, "glycan" is a sugar, which can be monomers or polymers of sugar residues, such as at least three sugars, and can be linear or branched. A "glycan" can include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a polypeptide, glycolipid, proteoglycan, etc.). The term also encompasses free glycans, including glycans that have been cleaved or otherwise released from a glycoconjugate.

As used herein, the term "glycoprotein" refers to a protein that contains a peptide backbone covalently linked to one or more sugar moieties (i.e., glycans). The sugar moiety(ies) may be in the form of monosaccharides, disaccharides, oligosaccharides, and/or polysaccharides. The sugar moiety (ies) may comprise a single unbranched chain of sugar residues or may comprise one or more branched chains. Glycoproteins can contain O-linked sugar moieties and/or N-linked sugar moieties.

As used herein, "immune-related thrombocytopenia" refers to disorders in which there is a relative decrease of platelets in the blood caused by increased destruction of platelets by the immune system. Non-limiting examples of immune-related thrombocytopenia disorders include idiopathic thrombocytopenic purapura, neonatal alloimmune thrombocytopenia, post-transfusion purapura, and systemic lupus erythematosus related thrombocytopenia.

As used herein, "IVIg" is a preparation of pooled, polyvalent IgG, including all four IgG subgroups, extracted from plasma of at least 1,000 human donors. IVIg is approved as a plasma protein replacement therapy for immune deficient patients. The level of IVIg Fc glycan sialylation varies between about 10-20% among IVIg preparations. As used herein, the term "derived from IVIg" refers to polypeptides which result from manipulation of IVIg. For example, polypeptides purified from IVIg (e.g., enriched for sialylated IgGs, modified IVIg (e.g., IVIg IgGs enzymatically sialylated), or Fc regions of IVIg (e.g., papain digested and sialylated) are derived from IVIg.

As used herein, an "N-glycosylation site of an Fc polypeptide" refers to an amino acid residue within an Fc polypeptide to which a glycan is N-linked. In some embodiments, an Fc region contains a dimer of Fc polypeptides, and the Fc region comprises two N-glycosylation sites, one on each Fc polypeptide.

As used herein "percent (%) of branched glycans" refers to the number of moles of glycan X relative to total moles of glycans present, wherein X represents the glycan of interest.

As used herein "percent (%) sequence identity" with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. Gaps can be introduced in one or both of a first and a second amino acid or nucleic acid sequence for optimal alignment and non-homologous sequences can be disregarded for comparison purposes. Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances a product will include amino acid variants, e.g., species that differ at terminal residues, e.g., at one, two, three, or four N-terminal residues and/or one C-terminal residue. In instances of such cases the sequence identity which is compared is the identity between the primary amino acid sequences of the most abundant active species in each of the products being compared. In some instances sequence identity refers to the amino acid sequence encoded by a nucleic acid that can be used to make the product.

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

"Pharmaceutical preparations" and "pharmaceutical products" can be included in kits containing the preparation or product and instructions for use.

"Pharmaceutical preparations" and "pharmaceutical products" generally refer to compositions in which the final predetermined level of sialylation has been achieved, and which are free of process impurities. To that end, "pharmaceutical preparations" and "pharmaceutical products" are substantially free of ST6Gal sialyltransferase and/or sialic acid donor (e.g., cytidine 5'-monophospho-N-acetyl neuraminic acid) or the byproducts thereof (e.g., cytidine 5'-monophosphate).

"Pharmaceutical preparations" and "pharmaceutical products" are generally substantially free of other components of a cell in which the glycoproteins were produced (e.g., the endoplasmic reticulum or cytoplasmic proteins and RNA), if recombinant.

As used herein, "polynucleotide" (or "nucleotide sequence" or "nucleic acid molecule") refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, "polypeptide" (or "amino acid sequence" or "protein") refers to a glycoprotein, oligopeptide, peptide, polypeptide, or protein sequence, and fragments or portions thereof, and to naturally occurring or synthetic molecules. "Amino acid sequence" and like terms, such as "polypeptide" or "protein," are not meant to limit the indicated amino acid sequence to the complete, native amino acid sequence associated with the recited protein molecule.

"Predetermined level" as used herein, refers to a pre-specified particular level of one or more particular glycans, e.g., branched glycans having a sialic acid on an α1,3 arm, and/or branched glycans having a sialic acid on an α1,6 arm, and/or branched glycans having a sialic acid on an α1,3 arm and on an α1,6 arm. In some embodiments, a predetermined level is an absolute value or range. In some embodiments, a predetermined level is a relative value. In some embodiments, a predetermined level is the same as or different (e.g., higher or lower than) a level of one or more particular glycans (e.g., branched glycans having a sialic acid on an α1,3 arm, and/or branched glycans having a sialic acid on an α1,6 arm, and/or branched glycans having a sialic acid on an α1,3 arm and on an α1,6 arm) in a reference, e.g., a reference polypeptide product, or a level specified in a reference document such as a pharmaceutical specification, a monograph, alert limit, or master batch record for a pharmaceutical product.

In some embodiments, a predetermined level is an absolute level or range of (e.g., number of moles of) one or more glycans (e.g., branched glycans having a sialic acid on an α1,3 arm, and/or branched glycans having a sialic acid on an α1,6 arm, and/or branched glycans having a sialic acid on an α1,3 arm and on an α1,6 arm) in a polypeptide preparation. In some embodiments, a predetermined level is a level or range of one or more glycans (e.g., branched glycans having a sialic acid on an α1,3 arm, and/or branched glycans having a sialic acid on an α1,6 arm, and/or branched glycans having a sialic acid on an α1,3 arm and on an α1,6 arm) in a polypeptide preparation relative to total level of glycans in the polypeptide preparation. In some embodiments, a predetermined level is a level or range of one or more glycans (e.g., branched glycans having a sialic acid on an α1,3 arm, and/or branched glycans having a sialic acid on an α1,6 arm, and/or branched glycans having a sialic acid on an α1,3 arm and on an α1,6 arm) in a polypeptide preparation relative to total level of sialylated glycans in the polypeptide preparation. In some embodiments, a predetermined level is expressed as a percent.

By "purified" (or "isolated") refers to a polynucleotide or a polypeptide that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acids. An isolated polynucleotide or polypeptide can be at least 60% free, or at least 75% free, or at least 90% free, or at least 95% free from other components present in natural environment of the indicated polynucleotide or polypeptide.

"Reference polypeptide" refers to a polypeptide having substantially the same amino acid sequence as (e.g., having about 95-100% identical amino acids of) a polypeptide described herein, e.g., a polypeptide to which it is compared. In some embodiments, a reference polypeptide is a therapeutic polypeptide described herein, e.g., an FDA approved therapeutic polypeptide.

As used herein, the term "sialylated" refers to a glycan having a terminal sialic acid. The term "mono-sialylated" refers to branched glycans having one terminal sialic acid, e.g., on an α1,3 arm or an α1,6 arm. The term "di-sialylated" refers to a branched glycan having a terminal sialic acid on two arms, e.g., both an α1,3 arm and an α1,6 arm.

As used herein, the term "ST6 sialyltransferase" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in transfer of a sialic acid to a terminal galactose of a glycan through an α2,6 linkage (e.g., ST6 Gal-I). A wide variety of ST6 sialyltransferase sequences are known in the art, such as those described herein; in some embodiments, an ST6 sialyltransferase shares at least one characteristic sequence of and/or shows the specified degree of overall sequence identity with one of the ST6 sialyltransferases set forth herein (each of which may be considered a "reference" ST6 sialyltransferase). In some embodiments, an ST6 sialyltransferase as described herein shares at least one biological activity with a reference ST6 sialyltransferase as set forth herein. In some such embodiment, the shared biological activity relates to transfer of a sialic acid to a glycan.

The term "subject," as used herein, means any subject for whom diagnosis, prognosis, or therapy is desired. In one embodiment, the subject is a human.

The term "thrombopoietin receptor agonist," as used herein, refers to pharmaceutical agents that stimulate platelet production in the bone marrow through interaction with the thrombopoietin receptor.

The term "treatment" or "treating," as used herein, refers to administering a therapy in an amount, manner, and/or mode effective to improve a condition, symptom, or parameter associated with a disorder or condition or to prevent or reduce progression of a disorder or condition to a degree detectable to one skilled in the art. An effective amount, manner, or mode can vary depending on the subject and may be tailored to the subject. The term "not being treated," as used herein, means a subject is not currently being administered a therapy.

As used herein, the terms "coupled," "linked," "joined," "fused," and "fusion" are used interchangeably. These terms refer to the joining together of two more elements or components by whatever means, including chemical conjugation or recombinant means.

While the present disclosure provides exemplary units and methods for the evaluation, identification, and production methods disclosed herein, a person of ordinary skill in the art will appreciate that performance of the evaluation, identification, and production methods herein is not limited to use of those units and/or methods. For example, "percent of branched glycans" provided herein are generally described, as a value for a glycan or structure relative to total glycan or structure on a mol/mol basis. A person of skill in the art understands that although the use of other metrics or units (e.g., mass/mass, mole percent vs. weight percent) to measure a described parameter might give rise to different absolute values than those described herein, a test preparation meets a disclosed target value even if other units or metrics are used, as long as the test preparation meets the herein disclosed value when the herein disclosed units and metrics are used, e.g., allowing for the sensitivity (e.g., analytical variability) of the method being used to measure the value.

I. Polypeptides

Examples of an Fc region-containing polypeptide preparation include, e.g., a preparation of Fc fragments, a preparation of antibody molecules, a preparation of Fc-fusion proteins (e.g., an Fc-receptor fusion protein), and a preparation of pooled, polyvalent immunoglobulin molecules (e.g., IVIg). Fc region-containing polypeptides may be recombinant or naturally derived.

Naturally derived polypeptides that can be used in the methods of the invention include, for example, intravenous immunoglobulin (IVIg) and polypeptides derived from IVIg (e.g., polypeptides purified from IVIg (e.g., enriched for sialylated IgGs), modified IVIg (e.g., IVIg IgGs enzymatically sialylated), or Fc regions of IVIg (e.g., papain digested and sialylated)).

Recombinant Fc region-containing polypeptides that can be used in the methods of the invention can be, for example, expressed in and purified from CHO cells and sialylated using human ST6-Gal sialtransferase enzyme (expressed in and purified from *E. coli* cells) or expressed in and purified from CHO cells and sialylated using human ST6-Gal sialtransferase enzyme (expressed in and purified from CHO cells).

A. N-Linked Glycosylation

N-linked oligosaccharide chains are added to a protein in the lumen of the endoplasmic reticulum. Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains three glucose, nine mannose, and two N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues. One of the branches is referred to in the art as the "α 1,3 arm," and the second branch is referred to as the "α 1,6 arm," as denoted in FIG. 1.

N-glycans can be subdivided into three distinct groups called "high mannose type," "hybrid type," and "complex type," with a common pentasaccharide core (Man (α 1,6)-(Man(α 1,3))-Man(β 1,4)-GlcpNAc(β 1,4)-GlcpNAc(β 1,N)-Asn) occurring in all three groups.

After initial processing in the endoplasmic reticulum, the polypeptide is transported to the Golgi where further processing may take place. If the glycan is transferred to the Golgi before it is completely trimmed to the core pentasaccharide structure, it results in a "high-mannose glycan."

Additionally or alternatively, one or more monosaccharides units of N-acetylglucosamine may be added to the core mannose subunits to form a "complex glycan." Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

Sialic acids are a family of 9-carbon monosaccharides with heterocyclic ring structures. They bear a negative charge via a carboxylic acid group attached to the ring as well as other chemical decorations including N-acetyl and N-glycolyl groups. The two main types of sialyl residues found in polypeptides produced in mammalian expression systems are N-acetyl-neuraminic acid (NeuAc) and N-glycolylneuraminic acid (NeuGc). These usually occur as terminal structures attached to galactose (Gal) residues at the non-reducing termini of both N- and O-linked glycans. The glycosidic linkage configurations for these sialyl groups can be either α 2,3 or α 2,6.

Fc regions are glycosylated at conserved, N-linked glycosylation sites. For example, each heavy chain of an IgG antibody has a single N-linked glycosylation site at Asn297 of the $C_H2$ domain. IgA antibodies have N-linked glycosylation sites within the $C_H2$ and $C_H3$ domains, IgE antibodies have N-linked glycosylation sites within the $C_H3$ domain, and IgM antibodies have N-linked glycosylation sites within the $C_H1$, $C_H2$, $C_H3$, and $C_H4$ domains.

Each antibody isotype has a distinct variety of N-linked carbohydrate structures in the constant regions. For example, IgG has a single N-linked biantennary carbohydrate at Asn297 of the $C_H2$ domain in each Fc polypeptide of the Fc region, which also contains the binding sites for C1q and FcγR. For human IgG, the core oligosaccharide normally consists of $GlcNAc_2Man_3GlcNAc$, with differing numbers of outer residues. Variation among individual IgG can occur via attachment of galactose and/or galactose-sialic acid at one or both terminal GlcNAc or via attachment of a third GlcNAc arm (bisecting GlcNAc).

B. Antibodies

Figure 2:
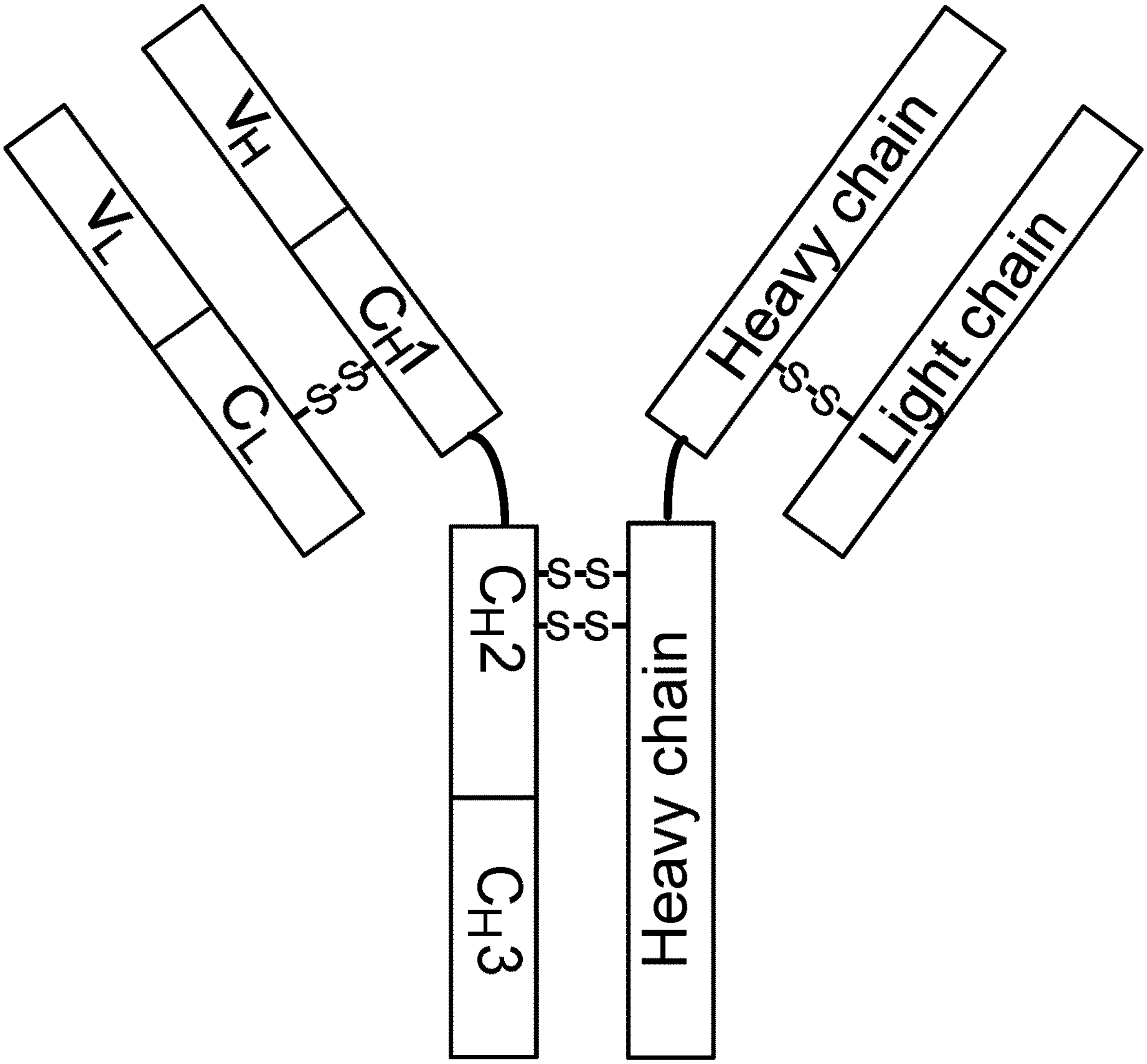
FIG. 2 is a schematic illustration of an IgG antibody molecule.

The basic structure of an IgG antibody is illustrated in FIG. 2. As shown in FIG. 2, an IgG antibody consists of two identical light polypeptide chains and two identical heavy polypeptide chains linked together by disulphide bonds. The first domain located at the amino terminus of each chain is variable in amino acid sequence, providing the antibody binding specificities found in each individual antibody. These are known as variable heavy ($V_H$) and variable light ($V_L$) regions. The other domains of each chain are relatively invariant in amino acid sequence and are known as constant heavy ($C_H$) and constant light ($C_L$) regions. As shown in FIG. 2, for an IgG antibody, the light chain includes one variable region ($V_L$) and one constant region ($C_L$). An IgG heavy chain includes a variable region ($V_H$), a first constant region ($C_H1$), a hinge region, a second constant region ($C_H2$), and a third constant region ($C_H3$). In IgE and IgM antibodies, the heavy chain includes an additional constant region ($C_H4$).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA, or IgY), class (e.g., IgG1, IgG2, IgG3, IgG4, IgA1, or IgA2) or subclass.

The term "Fc fragment," as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a $F(ab')_2$ fragment, a Fd fragment, a Fv fragment, a scFv fragment, a dAb fragment (Ward et al., (1989) Nature 341:544-546), and an isolated complementarily determining region (CDR). These antibody fragments can be obtained using conventional techniques known to those with skill in the art, and the fragments can be screened for utility in the same manner as are intact antibodies.

Reference Fc region-containing polypeptides described herein can be produced by any method known in the art for the synthesis of antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645).

Additional reference Fc region-containing polypeptides described herein are bispecific antibodies and multivalent antibodies, as described in, e.g., Segal et al., J. Immunol. Methods 248:1-6 (2001); and Tutt et al., J. Immunol. 147: 60 (1991).

C. Polypeptide Conjugates

The disclosure includes polypeptides (or Fc regions or Fc fragments thereof containing one or more N-glycosylation sites) that are conjugated or fused to one or more heterologous moieties and that have different levels of sialylated glycans relative to a corresponding reference polypeptide. Heterologous moieties include, but are not limited to, peptides, polypeptides, proteins, fusion proteins, nucleic acid molecules, small molecules, mimetic agents, synthetic drugs, inorganic molecules, and organic molecules. In some instances, a reference polypeptide is a fusion protein that comprises a peptide, polypeptide, protein scaffold, scFv, dsFv, diabody, Tandab, or an antibody mimetic fused to an Fc region, such as a glycosylated Fc region. The fusion protein can include a linker region connecting the Fc region to the heterologous moiety (see, e.g., Hallewell et al. (1989), J. Biol. Chem. 264, 5260-5268; Alfthan et al. (1995), Protein Eng. 8, 725-731; Robinson & Sauer (1996)).

In some instances, a reference fusion protein includes an Fc region (or an Fc fragment containing one or more N-glycosylation sites thereof) conjugated to a heterologous polypeptide of at least 10, at least 20, at least 30, at least 40, at least 50, at least 60, at least 70, at least 80, at least 90, or at least 100 amino acids.

In some instances, a reference fusion protein can include an Fc region (or Fc fragment containing one or more N-glycosylation sites thereof) conjugated to marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, a reference polypeptide (or an Fc region or Fc fragment containing one or more N-glycosylation sites thereof) is conjugated to a diagnostic or detectable agent. Such fusion proteins can be useful for monitoring or prognosing the development or progression of disease or disorder as part of a clinical testing procedure, such as determining the efficacy of a particular therapy. Such diagnosis and detection can be accomplished by coupling the polypeptide to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C), sulfur ($^{35}$S), tritium ($^{3}$H), indium ($^{15}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn, and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

D. Sialyltransferase Polypeptides

Methods and compositions described herein include the use of a sialyltransferase enzyme, e.g., an a 2,6 sialyltransferase (e.g., ST6 Gal-I). A number of ST6 sialyltransferases are known in the art and are commercially available (see, e.g., Takashima, Biosci. Biotechnol. Biochem. 72:1155-1167 (2008); Weinstein et al., J. Biol. Chem. 262:17735-17743 (1987)). ST6 Gal-I catalyzes the transfer of sialic acid from a sialic acid donor (e.g., cytidine 5'-monophospho-N-acetyl neuraminic acid) to a terminal galactose residue of glycans through an α 2,6 linkage. The sialic acid donor reaction product is cytidine 5-monophosphate. FIGS. 3A-3C depict three exemplary ST6 sialyltransferase amino acid sequences (SEQ ID NOs:1-3). In some embodiments, an ST6 sialyltransferase has or includes an amino acid sequence set forth in SEQ ID NO:1, SEQ ID NO:2, or in amino acid residues 95-416 of SEQ ID NO:3, or a characteristic sequence element thereof or therein. In some embodiments, an ST6 sialyltransferase has at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, SEQ ID NO:2, or amino acid residues 95-416 of SEQ ID NO:3. Alternatively or additionally, in some embodiments, an ST6 sialyltransferase includes at least about 5, 10, 15, 20, 25, 30, 35, 40, 45, 50, 75, 100, or 150 or more contiguous amino acid residues found in SEQ ID NO:1, SEQ ID NO:2, or amino acid residues 95-416 of SEQ ID NO:3.

In some embodiments, an ST6 sialyltransferase differs from an amino acid sequence as set forth in SEQ ID NO:1, SEQ ID NO:2, or in amino acid residues 95-416 of SEQ ID NO:3, or characteristic sequence elements thereof or therein, by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, an ST6 sialyltransferase polypeptide includes a substituent group on one or more amino acid residues. Still other useful polypeptides are associated with (e.g., fused, linked, or coupled to) another moiety (e.g., a peptide or molecule). For example, an ST6 sialyltransferase polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide).

II. Methods for Producing Sialylated Polypeptides

The present disclosure relates to Fc region-containing polypeptide preparations (e.g., IVIg, Fc, or IgG antibodies) having higher levels of branched glycans that are sialylated on an α 1,3 and 1,6 arm of the branched glycans in the Fc region (e.g., with a NeuAc-α 2,6-Gal or NeuAc-α 2,3-Gal terminal linkage), relative to a corresponding reference polypeptide preparation. The higher levels can be measured on an individual Fc region (e.g., an increase in the number of branched glycans that are sialylated on an α 1,3 arm of the branched glycans in the Fc region), or the overall composition of a preparation of polypeptides can be different (e.g., a preparation of polypeptides can have a higher number or a higher percentage of branched glycans that are sialylated on an α 1,3 arm and an α 1,6 arm of the branched glycans in the Fc region) relative to a corresponding preparation of reference polypeptides).

In exemplary methods, Fc molecules were obtained or produced from various sources, glycan compositions were characterized, and activities were determined. The Fc molecules were tested for their ability to increase reticulated platelets in immune-related thrombocytopenia models.

Figure 4:
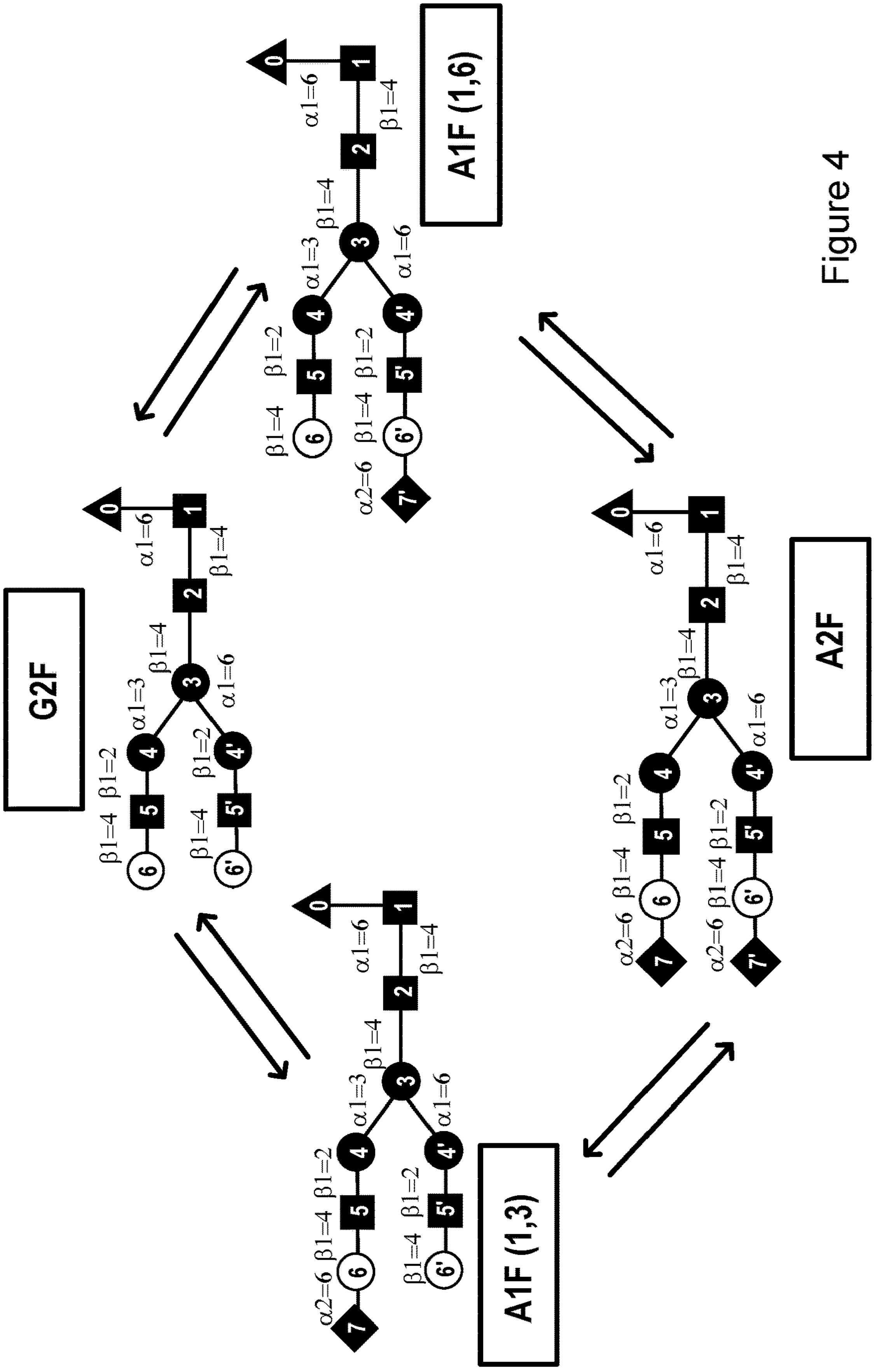
FIG. 4 is a schematic illustration of a reaction scheme for ST6 sialyltransferase (fucose: triangles, N-acetylglucosamine: squares, mannose: dark circles, galactose: light circles, sialic acid: diamonds).

ST6 Gal-I sialyltransferase catalyzes the transfer of sialic acid from a sialic acid donor (e.g., cytidine 5'-monophospho-N-acetyl neuraminic acid) to a terminal galactose residue of glycans through an α 2,6 linkage. The present disclosure exploits the discovery that ST6 sialyltransferase catalyzes the transfer of sialic acid to branched glycans (e.g., Fc branched glycans) comprising an α 1,3 arm and an α 1,6 arm in an ordered fashion. As shown in FIG. 4, ST6 sialyltransferase transfers a sialic acid to an α 1,3 arm of a branched glycan, which can be followed by transfer of a second sialic acid to an α 1,6 arm (yielding a disialylated branched glycan), and can further be followed by removal of sialic acid from an α 1,3 arm (yielding a branched glycan having a sialic acid on an α 1,6 arm). Accordingly, by controlling and/or modulating activity (e.g., kinetics) of ST6 sialyltransferase, polypeptides having particular sialylation patterns can be produced.

Any parameter generally known to affect enzyme kinetics can be controlled and/or modulated to produce a polypeptide preparation having a predetermined level of sialic acid on an α 1,3 arm of a branched glycan, on an α 1,6 arm of a branched glycan, and/or on an α 1,3 arm and an α 1,6 arm of a branched glycan. For example, reaction time, ST6 sialyltransferase concentration and/or specific activity, branched glycan concentration, sialic acid donor concentration, sialic acid donor reaction product concentration, pH, buffer composition, and/or temperature can be controlled and/or modulated to produce a polypeptide preparation having a desired level of sialylation (e.g., α 1,3 arm and/or α 1,6 arm sialylation).

In some embodiments, to preferentially sialylate an α1,3 arm of branched glycans (e.g., having an a 1,3 arm and an α 1,6 arm), branched glycans are contacted in vitro with an ST6 sialyltransferase under limited reaction conditions. Such limited reaction conditions are selected such that addition of a sialic acid to an α 1,3 arm is enhanced relative to addition of a sialic acid to an α 1,6 arm (e.g., rate of transfer of a sialic acid to an α 1,3 arm ("$R_a^{1,3}$") exceeds rate of transfer of a sialic acid to an α 1,6 arm ("$R_a^{1,6}$"). In some embodiments, limited reaction conditions are further selected such that removal of a sialic acid from an α1,6 arm is enhanced relative to addition of a sialic acid to an α 1,6 arm (e.g., rate of removal of a sialic acid from an α 1,6 arm ("$R_r^{1,6}$") exceeds rate of transfer of a sialic acid to an α 1,6 arm ("$R_a^{1,6}$"). Limited reaction conditions can include, for example, reduced reaction time, reduced enzyme concentration and/or activity, reduced amount of branched glycans, reduced level of sialic acid donor, and/or reduced temperature.

In some embodiments, to preferentially sialylate an α1,6 arm of branched glycans (e.g., having an α 1,3 arm and an α 1,6 arm), branched glycans can be contacted in vitro with an ST6 sialyltransferase under extended reaction conditions. Such extended reaction conditions are selected such that addition of a sialic acid to an α 1,6 arm is enhanced relative to removal of a sialic acid from an α 1,6 arm (e.g., rate of transfer of a sialic acid to an α 1,6 arm ("$R_a^{1,6}$") exceeds rate of removal of a sialic acid from an α 1,6 arm ("$R_r^{1,6}$")). In some embodiments, extended reaction conditions are further selected such that, after initial conditions that enhance addition of sialic acid to an α 1,3 arm, conditions are extended such that removal of a sialic acid from an α 1,3 arm is eventually enhanced relative to addition of a sialic acid to an α 1,3 arm (e.g., rate of removal of a sialic acid from an α 1,3 arm ("$R_r^{1,3}$") exceeds rate of transfer of a sialic acid to an α 1,3 arm ("$R_a^{1,3}$")). Extended reaction conditions can include, for example, increased reaction time, increased enzyme concentration and/or activity, increased amount of branched glycans, increased level of sialic acid donor, and/or increased temperature.

In some embodiments, to preferentially sialylate both an α 1,3 arm and an α 1,6 arm of branched glycans (e.g., having an α 1,3 arm and an α 1,6 arm), branched glycans are contacted in vitro with an ST6 sialyltransferase under intermediate reaction conditions. Such intermediate reaction conditions are selected such that addition of a sialic acid to an α 1,3 arm is enhanced relative to removal of a sialic acid from an α 1,3 arm (e.g., rate of transfer of a sialic acid to an α 1,3 arm ("$R_a^{1,3}$") exceeds rate of removal of a sialic acid from an α 1,3 arm ("$R_r^{1,3}$"). In some embodiments, intermediate reaction conditions are further selected such that addition of a sialic acid to an α 1,6 arm is enhanced relative to removal of a sialic acid from an α 1,6 arm (e.g., rate of addition of a sialic acid to an α 1,6 arm ("$R_a^{1,6}$") exceeds rate of removal of a sialic acid from an α 1,6 arm ("$R_r^{1,6}$"). Intermediate reaction conditions can include, for example, intermediate reaction time, intermediate enzyme concentration and/or activity, intermediate amount of branched glycans, intermediate level of sialic acid donor, and/or intermediate temperature. In some embodiments, intermediate reaction conditions further include supplementing the sialic acid donor at least once during the reaction. In some embodiments, intermediate reaction conditions further include removing a sialic acid donor reaction product at least once during the reaction. In some embodiments, intermediate reaction conditions further include supplementing the sialic acid donor reaction product at least once during the reaction.

In some embodiments, a polypeptide, e.g., a glycosylated antibody, is sialylated after the polypeptide is produced. For example, a polypeptide can be recombinantly expressed in a host cell (as described herein) and purified using standard methods. The purified polypeptide is then contacted with an ST6 sialyltransferase (e.g., a recombinantly expressed and purified ST6 sialyltransferase) in the presence of reaction conditions as described herein. In certain embodiments, the conditions include contacting the purified polypeptide with an ST6 sialyltransferase in the presence of a sialic acid donor, e.g., cytidine 5'-monophospho-N-acetyl neuraminic acid, manganese, and/or other divalent metal ions. In some embodiments, IVIg is used in a sialylation method described herein.

In some embodiments, chemoenzymatic sialylation is used to sialylate polypeptides. Briefly, this method involves sialylation of a purified branched glycan, followed by incorporation of the sialylated branched glycan en bloc onto a polypeptide to produce a sialylated polypeptide.

A branched glycan can be synthesized de novo using standard techniques or can be obtained from a polypeptide preparation (e.g., a recombinant polypeptide, Fc, or IVIg) using an appropriate enzyme, such as an endoglycosidase (e.g., EndoH or EndoF). After sialylation of the branched glycan, the sialylated branched glycan can be conjugated to a polypeptide using an appropriate enzyme, such as a transglycosidase, to produce a sialylated polypeptide.

In one exemplary method, a purified branched N-glycan is obtained from a polypeptide (e.g., a polypeptide preparation, e.g., IVIg) using an endoglycosidase. The purified branched N-glycan is then chemically activated on the reducing end to form a chemically active intermediate. The branched N-glycan is then further processed, trimmed, and/or glycosylated using appropriate known glycosidases. The branched glycan is then sialylated using an ST6 sialylation as described herein. After engineering, the desired branched N-glycan is transferred onto a polypeptide using a transglycosidase (such as a transglycosidase in which glycosidic activity has been attenuated using genetically engineering).

In some embodiments, a branched glycan used in methods described herein is a galactosylated branched glycan (e.g., includes a terminal galactose residue). In some embodiments, a branched glycan is galactosylated before being sialylated using a method described herein. In some embodiments, a branched glycan is first contacted with a galactosyltransferase (e.g., a beta-1,3-galactosyltransferase) and subsequently contacted with an ST6 sialyltransferase as described herein. In some embodiments, a galactosylated glycan is purified before being contacted with an ST6 sialyltransferase. In some embodiments, a galactosylated glycan is not purified before being contacted with an ST6 sialyltransferase. In some embodiments, a branched glycan is contacted with a galactosyltransferase and an ST6 sialyltransferase in a single step.

In some embodiments, a host cell is genetically engineered to express a polypeptide described herein and one or more sialyltransferase enzymes, e.g., an ST6 sialyltransferase. In some embodiments, the host cell is genetically engineered to further express a galactosyltransferase. The genetically engineered host cell can be cultured under conditions sufficient to produce a particular sialylated polypeptide. For example, to produce polypeptides preferentially sialylated on α1,3 arms of branched glycans, a host cell can be genetically engineered to express a relatively low level of ST6 sialyltransferase, whereas to produce polypeptides preferentially sialylated on α1,6 arms of branched glycans, a host cell can be genetically engineered to express a relatively high level of ST6 sialyltransferase. In some embodiments, to produce polypeptides preferentially sialylated on α1,3 arms of branched glycans, a genetically engineered host cell can be cultured in a relatively low level of sialic acid donor, whereas to produce polypeptides preferentially sialylated on α1,6 arms of branched glycans, a genetically engineered host cell can be cultured in a relatively high level of sialic acid donor.

Recombinant expression of a gene, such as a nucleic acid encoding a reference polypeptide and/or a sialtransferase described herein, can include construction of an expression vector containing a polynucleotide that encodes a reference polypeptide and/or a sialtransferase. Once a polynucleotide has been obtained, a vector for the production of the reference polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then cultured by conventional techniques to produce reference polypeptides.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the *E. coli* expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by the inclusion of appropriate transcription enhancer elements, transcription terminators, etc. (see, e.g., Bittner et al., 1987, Methods in Enzymol. 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7030 and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

In some embodiments, a reference Fc region-containing polypeptide is recombinantly produced in cells as described herein, purified, and contacted with a sialtransferase enzyme in vitro to produce Fc region-containing polypeptides containing higher levels of glycans having higher levels of sialic acid on the α 1,3 arms and α 1,6 arms of the branched glycans with a NeuAc-α 2,6-Gal terminal linkage, relative to the reference polypeptide. In some embodiments, a purified reference polypeptide is contacted with the sialtransferase in the presence of CMP-sialic acid, manganese, and/or other divalent metal ions.

A reference Fc region-containing polypeptide can be purified by any method known in the art for purification, for example, by chromatography (e.g., ion exchange, affinity, and sizing column chromatography), centrifugation, differential solubility, or by any other standard technique for the purification of proteins. For example, a reference antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a reference polypeptide can be fused to heterologous polypeptide sequences to facilitate purification.

In some embodiments, a polypeptide can be purified using a lectin column by methods known in the art (see, e.g., WO 02/30954). For example, a preparation of polypeptides can be enriched for polypeptides containing glycans having sialic acids in α 2,6 linkage as described in, e.g., WO2008/057634. Following enrichment of polypeptides containing glycans having sialic acids in α 2,6 linkage, the glycan composition of such polypeptides can be further characterized to identify polypeptides having sialic acids attached to the α 1,3 arm and α 1,6 arm of a branched glycan. Preparations of polypeptides containing a predetermined level of glycans having sialic acids in α 2,6 linkage on the α 1,3 arm and α 1,6 arm can be selected for use, e.g., for therapeutic use. Such compositions can have increased levels of anti-inflammatory activity.

In accordance with the present disclosure, there may be employed conventional molecular biology, microbiology, and recombinant DNA techniques within the skill of the art. Such techniques are described in the literature (see, e.g., Green & Sambrook, Molecular Cloning: A Laboratory Manual, Fourth Edition (2012) Cold Spring Harbor Laboratory Press, Cold Spring Harbor, N.Y.; DNA Cloning: A Practical Approach, Volumes I and II (Glover and Hames, eds. 1995); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); R. I. Freshney, Culture of Animal Cells: A Manual of Basic Technique and Specialized Application (2010); Immobilized Cells and Enzymes (IRL Press, (1986)); J. M. Guisan, Immobilization of Enzymes and Cells (2013); B. Perbal, A Practical Guide To Molecular Cloning (1984); T. A. Brown, Essential Molecular Biology: A Practical Approach Volume I (2000); T. A. Brown, Essential Molecular Biology: A Practical Approach Volume II (2002); F. M. Ausubel et al. (eds.), Current Protocols in Molecular Biology, John Wiley & Sons, Inc. (1994).

Glycan compositions can be characterized using methods described in, e.g., Barb, Biochemistry 48:9705-9707 (2009); Anumula, J. Immunol. Methods 382:167-176 (2012); Gilar et al., Analytical Biochem. 417:80-88 (2011).

Glycan Evaluation

Glycans of polypeptides can be evaluated using any methods known in the art. For example, sialylation of glycan compositions (e.g., level of branched glycans that are sialylated on an α1,3 arm and/or an α1,6 arm) can be characterized using methods described in, e.g., Barb, Biochemistry 48:9705-9707 (2009); Anumula, J. Immunol. Methods 382: 167-176 (2012); Gilar et al., Analytical Biochem. 417:80-88 (2011); Wuhrer et al., J. Chromatogr. B. 849:115-128 (2007). In some embodiments, in addition to evaluation of sialylation of glycans, one or more parameters described in Table 1 are evaluated.

In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a polypeptide preparation with one or more enzymes under conditions and for a time sufficient to release one or more glycan(s) (e.g., one or more exposed glycan(s)). In some instances, the one or more enzymes include(s) PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1 D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or polypeptides. For example, in certain instances, glycans are analyzed in accordance with the present disclosure using one or more available methods (to give but a few examples, see *Anumula, Anal. Biochem.,* 350(1):1, 2006; Klein et al., *Anal. Biochem.,* 179:162, 1989; and/or Townsend, R. R. Carbohydrate Analysis" High Performance Liquid Chromatography and Capillary Electrophoresis, Ed. Z. El Rassi, pp 181-209, 1995; WO2008/128216; WO2008/128220; WO2008/128218; WO2008/130926; WO2008/128225; WO2008/130924; WO2008/128221; WO2008/128228; WO2008/128227; WO2008/128230; WO2008/128219; WO2008/128222; WO2010/071817; WO2010/071824; WO2010/085251; WO2011/069056; and WO2011/127322, each of which is incorporated herein by reference in its entirety). For example, in some instances, glycans are characterized using one or more of chromatographic methods, electrophoretic methods, nuclear magnetic resonance methods, and combinations thereof. In some instances, methods for evaluating one or more target protein specific parameters, e.g., in a polypeptide preparation, e.g., one or more of the parameters disclosed herein, can be performed by one or more of following methods.

TABLE 1

Exemplary methods of evaluating parameters:

| Method(s) | Relevant literature | Parameter |
|---|---|---|
| C18 UPLC Mass Spec.* | Chen and Flynn, Anal. Biochem., 370: 147-161 (2007)<br>Chen and Flynn, J. Am. Soc. Mass Spectrom., 20: 1821-1833 (2009) | Glycan(s)<br>(e.g., N-linked glycan, exposed N-linked glycan, glycan detection, glycan identification, and characterization; site specific glycation; glycoform detection (e.g., parameters 1-7); percent glycosylation; and/or aglycosyl) |

TABLE 1-continued

Exemplary methods of evaluating parameters:

| Method(s) | Relevant literature | Parameter |
|---|---|---|
| Peptide LC-MS (reducing/non-reducing) | Dick et al., Biotechnol. Bioeng., 100: 1132-1143 (2008)<br>Yan et al., J. Chrom. A., 1164: 153-161 (2007)<br>Chelius et al., Anal. Chem., 78: 2370-2376 (2006)<br>Miller et al., J. Pharm. Sci., 100: 2543-2550 (2011) | C-terminal lysine |
| LC-MS (reducing/non-reducing/alkylated) | Dick et al., Biotechnol. Bioeng., 100: 1132-1143 (2008)<br>Goetze et al., Glycobiol., 21: 949-959 (2011) | |
| Weak cation exchange (WCX) chromatography | Dick et al., Biotechnol. Bioeng., 100: 1132-1143 (2008) | |
| LC-MS (reducing/non-reducing/alkylated) | Dick et al., Biotechnol. Bioeng., 100: 1132-1143 (2008)<br>Goetze et al., Glycobiol., 21: 949-959 (2011) | N-terminal pyroglu |
| PeptideLC-MS (reducing/non-reducing) | Yan et al., J. Chrom. A., 1164: 153-161 (2007)<br>Chelius et al., Anal. Chem., 78: 2370-2376 (2006)<br>Miller et al., J. Pharm. Sci., 100: 2543-2550 (2011) | |
| Peptide LC-MS (reducing/non-reducing) | Yan et al., J. Chrom. A., 1164: 153-161 (2007);<br>Xie et al., mAbs, 2: 379-394 (2010) | Methionine oxidation |
| Peptide LC-MS (reducing/non-reducing) | Miller et al., J. Pharm. Sci., 100: 2543-2550 (2011) | Site specific glycation |
| Peptide LC-MS (reducing/non-reducing) | Wang et al., Anal. Chem., 83: 3133-3140 (2011);<br>Chumsae et al., Anal. Chem., 81: 6449-6457 (2009) | Free cysteine |
| Bioanalyzer (reducing/non-reducing)* | Forrer et al., Anal. Biochem., 334: 81-88 (2004) | Glycan (e.g., N-linked glycan, exposed N-linked glycan) (including, for example, glycan detection, identification, and characterization; site specific glycation; glycoform detection; percent glycosylation; and/or aglycosyl) |
| LC-MS (reducing/non-reducing/alkylated)*<br>* Methods include removal (e.g., enzymatic, chemical, and physical) of glycans | Dick et al., Biotechnol. Bioeng., 100: 1132-1143 (2008)<br>Goetze et al., Glycobiol., 21: 949-959 (2011)<br>Xie et al., mAbs, 2: 379-394 (2010) | Glycan (e.g., N-linked glycan, exposed N-linked glycan) (including, for example, glycan detection, identification, and characterization; site specific glycation; glycoform detection; percent glycosylation; and/or aglycosyl) |
| Bioanalyzer (reducing/non-reducing) | Forrer et al., Anal. Biochem., 334: 81-88 (2004) | Light chain: Heavy chain |
| Peptide LC-MS (reducing/non-reducing) | Yan et al., J. Chrom. A., 1164: 153-161 (2007)<br>Chelius et al., Anal. Chem., 78: 2370-2376 (2006)<br>Miller et al., J. Pharm. Sci., 100: 2543-2550 (2011) | Non-glycosylation-related peptide modifications (including, for example, sequence analysis and identification of sequence variants; oxidation; succinimide; aspartic acid; and/or site-specific aspartic acid) |
| Weak cation exchange (WCX) chromatography | Dick et al., Biotechnol. Bioeng., 100: 1132-1143 (2008) | Isoforms (including, for example, charge variants (acidic variants and basic variants); and/or deamidated variants) |
| Anion-exchange chromatography | Ahn et al., J. Chrom. B, 878: 403-408 (2010) | Sialylated glycan |
| Anion-exchange chromatography | Ahn et al., J. Chrom. B, 878: 403-408 (2010) | Sulfated glycan |
| 1,2-diamino-4,5-methylenedioxybenzene (DMB) labeling method | Hokke et al., FEBS Lett., 275: 9-14 (1990) | Sialic acid |
| LC-MS | Johnson et al., Anal. Biochem., 360: 75-83 (2007) | C-terminal amidation |
| LC-MS | Johnson et al., Anal. Biochem., 360: 75-83 (2007) | N-terminal fragmentation |
| Circular dichroism spectroscopy | Harn et al., Current Trends in Monoclonal Antibody Development and Manufacturing, S. J. Shire et al., eds, 229-246 (2010) | Secondary structure (including, for example, alpha helix content and/or beta sheet content) |

TABLE 1-continued

| Exemplary methods of evaluating parameters: | | |
|---|---|---|
| Method(s) | Relevant literature | Parameter |
| Intrinsic and/or ANS dye fluorescence | Harn et al., Current Trends in Monoclonal Antibody Development and Manufacturing, S. J. Shire et al., eds, 229-246 (2010) | Tertiary structure (including, for example, extent of protein folding) |
| Hydrogen-deuterium exchange-MS | Houde et al., Anal. Chem., 81: 2644-2651 (2009) | Tertiary structure and dynamics (including, for example, accessibility of amide protons to solvent water) |
| Size-exclusion chromatography | Carpenter et al., J. Pharm. Sci., 99: 2200-2208 (2010) | Extent of aggregation |
| Analytical ultracentrifugation | Pekar and Sukumar, Anal. Biochem., 367: 225-237 (2007) | |

References listed in Table 1 are hereby incorporated by reference in their entirety or, in the alternative, to the extent that they pertain to one or more of the methods disclosed in Table 1. Other methods for evaluating one or more parameters are disclosed in the examples.

III. Treatment of immune-related thrombocytopenia

The inventors have discovered that biological activity of Fc-containing molecules is enhanced by sialylation of two branches of branched glycans. Accordingly, Fc region-containing polypeptides described herein (e.g., Fc region-containing polypeptides containing glycans containing sialic acid on an α 1,3 arm and an α 1,6 arm of branched glycans with a NeuAc-α 2,6-Gal terminal linkage) have increased activity relative to a reference polypeptide. Current treatments for immune-related thrombocytopenia include IVIg infusions, platelets transfusions, and treatment with thrombopoietin or thrombopoietin receptor agonist, e.g., romiplostim (NPLATE@, Amgen) and eltrombopag (PROMACTA@, GlaxoSmithKline).

IV. Pharmaceutical Compositions and Administration

A polypeptide of the present disclosure, e.g., an Fc region-containing polypeptide comprising branched glycans that are sialylated on both an α 1,3 arm and an α 1,6 arm of the branched glycan in the Fc region, e.g., with a NeuAc-α 2,6-Gal terminal linkage, can be incorporated into a pharmaceutical composition and can be useful in the treatment of immune-related thrombocytopenia. Such a pharmaceutical composition is useful as an improved composition for the prevention and/or treatment of diseases relative to the corresponding reference polypeptide. Pharmaceutical compositions comprising a polypeptide can be formulated by methods known to those skilled in the art. The pharmaceutical composition can be administered parenterally in the form of an injectable formulation comprising a sterile solution or suspension in water or another pharmaceutically acceptable liquid. For example, the pharmaceutical composition can be formulated by suitably combining the sulfated polypeptide with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Non-limiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampoule.

Route of administration can be parenteral, for example, administration by injection, transnasal administration, transpulmonary administration, ortranscutaneous administration. Administration can be systemic or local by intravenous injection, intramuscular injection, intraperitoneal injection, subcutaneous injection.

The term "subcutaneous administration" refers to introduction of a drug under the skin of an animal or human patient (e.g., by subcutaneous infusion or subcutaneous bolus), preferably within a pocket between the skin and underlying tissue, by relatively slow, sustained delivery from a drug receptacle. The pocket may be created by pinching or drawing the skin up and away from underlying tissue. In particular embodiments, an extracellular matrix degrading enzyme (e.g., a hyaluronidase or any extracellular matrix degrading enzyme described herein) is administered at each of the sites (e.g., prior to administration of the composition and/or during the non-delivery period). In particular embodiments, the extracellular matrix degrading enzyme is co-infused with the composition.

Convenient sites for subcutaneous administration include the shoulder, upper arm, thigh, and abdomen. In particular embodiments of the above methods, the composition is administered into subcutis or fat at a depth between 2 mm and 10 mm below the dermis of the subject.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

The term "extracellular matrix degrading enzyme" means an enzyme that can break down extracellular matrix at the site of infusion, resulting in improved tissue permeability for an composition infused at the site. Extracellular matrix degrading enzymes include enzymes catalyzing the hydrolysis of hyaluronic acid (hyaluronan), a glycosaminoglycan, chondroitin, or collagen, such as a hyaluronidase, glycosaminoglycanase, collagenase (e.g. cathepsin), serine proteases, thiol proteases, and matrix metalloproteases, of which the human enzymes are preferred and the recombinant human enzymes are most preferred. Examples of such enzymes which can be used in the methods and compositions of the invention are described in U.S. Pat. Nos. 4,258,134; 4,820,516; 7,871,607; 7,767,429; 7,829,081; 7,846,431; 7,871,607; 8,187,855; and 8,105,586, and U.S. Patent Publication Nos. 20090304665; 20110053247; 20120101325; and 20110008309, each of which is incorporated by reference. Human hyaluronidases which can be used in the methods and compositions of the invention are also described, for example, in U.S. Pat. Nos. 3,945,889; 6,057,110; 5,958,750; 5,854,046; 5,827,721; and 5,747,027, each of which is incorporated herein by reference. Commercially available hyaluronidases which can be used in the methods and compositions of the invention include HYDASE™ (PrimaPharm Inc.), VITRASSE® (ISTA Pharmaceuticals), AMPHADASE® (Amphastar Pharmaceuticals), and HYLENEX® (sold by Halozyme Therapeutics).

A suitable means of administration can be selected based on the age and condition of the patient. A single dose of the pharmaceutical composition containing a modified polypeptide can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

EXAMPLES

Example 1—Preparation of Sialylated Glycoproteins

The sialylation of IVIg by the sialyltransferase ST6 was analyzed. IVIg was first galactosylated and then sialylated. The reactions were performed sequentially. There was no purification between galactosylation and sialylation reactions. The relative abundance of glycoforms was analyzed following the sialylation reactions.

Galactosylation

A reaction was set up that contained the following components at the concentrations indicated in Table 2:

TABLE 2

| Galactosylation conditions (Target s2IVIG) | |
|---|---|
| Constituent | Final concentration |
| MOPS (pH 7.4) | 50 mM |
| $MnCl_2$ | 8 mM |
| IVIg | 125 mg/ml |
| B4GalT1 (100 u/ml) | 1.04 mg/g-IVIG |
| UDP-Galactose | 5 mM |

The reaction was incubated for 24-72 hours at 37° C.

B. Sialylation

To an aliquot of the galactosylation reaction were added CMP-NANA, MOPS buffer and ST6Gal1.

The final volume was adjusted so that the final concentration of components in the reaction was as indicated in Table 3.

TABLE 3

| Sialylation conditions | |
|---|---|
| Constituent | Final concentration |
| MOPS (pH 7.4) | 50 mM |
| IVIg | 115 mg/ml |
| CMP-NANA (6 × 8 mM) | 48 mM |
| ST6Gal1 (SEQ ID NO: 1) | 3.5 mg/g-IVIg |

The reaction was incubated at 37° C. Aliquots were extracted at the times indicated in FIG. 5 and frozen at −20° C. for later analyses.

C. Results

Figure 5:
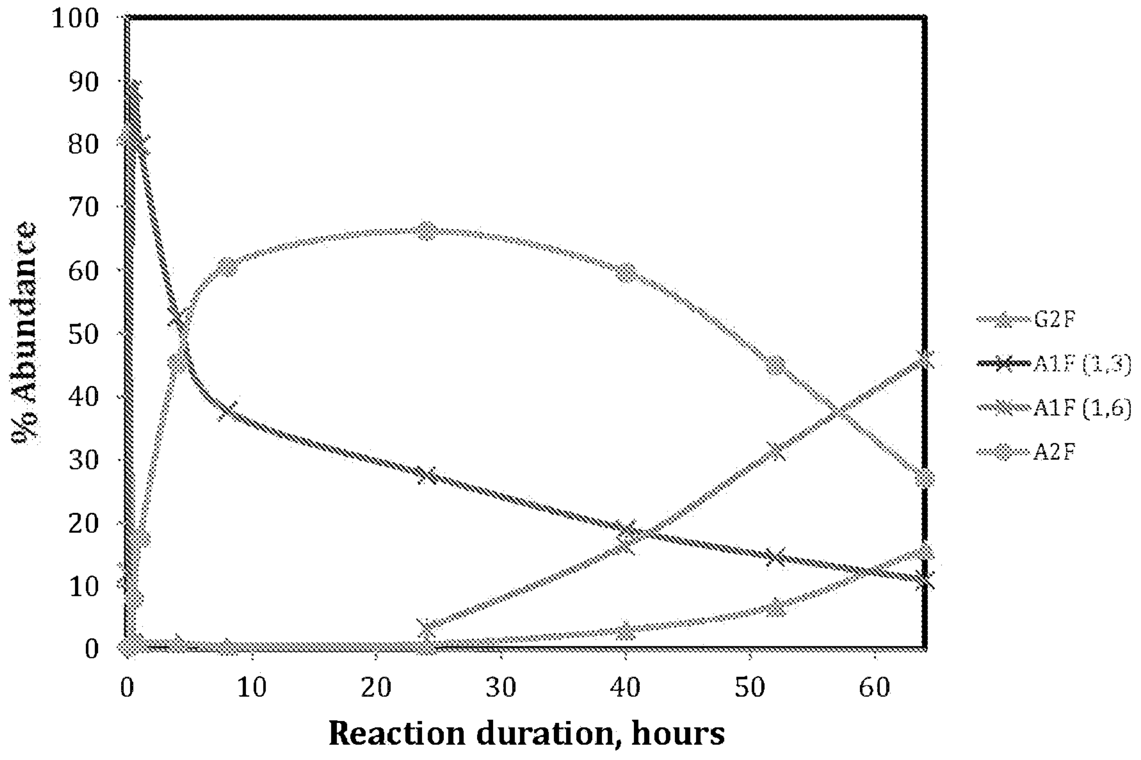
FIG. 5 is a graphic representation of relative abundance of glycans at various times during a sialylation reaction with ST6 sialyltransferase.

As shown in FIG. 5, the predominant glycoform changed over time from G2F to A1F (1,3) to A2F to A1F (1,6). The results are summarized in the reaction scheme depicted in FIG. 4. As shown in FIG. 4, the product glycoform can change between G2F, A1F (1,3), A2F, and A1F (1,6) during the course of a reaction due to competing addition (forward reaction) and removal (back reaction) steps.

The sialyltransferase ST6 can add sialic acid to either branch of a substrate's biantennary N-glycan. However, these results demonstrate that addition to each branch happens at different rates, resulting in different end products depending on the reaction conditions. Addition of sialic acid to the α1,3 branch is faster than addition to the α1,6 branch.

These data also demonstrate that sialyltransferase ST6 can also catalyze the removal of sialic acids from N-glycans. The removal of sialic acid from the α1,3 branch is faster than removal from the α1,6 branch. This can surprisingly lead to the production of Fc glycans substantially or primarily monosialylated on the α1,6 branch by modulating reaction conditions.

This Example demonstrates that reaction conditions can be controlled to produce a glycoprotein product having a predetermined or target sialylation levels. Such conditions can include time, ST6 sialyltransferase concentration, substrate concentration, donor sugar nucleotide concentration, product nucleotide concentration, pH, buffer composition, and/or temperature.

Example 2—Dose Response of IVIg, S1-IVIg, S2-IVIg, and Des-IVIg in a Chronic ITP Mouse Model The effect of IVIg, S1-IVIg, S2-IVIg, and Des-IVIg at varying doses in an anti-CD41 antibody mediated ITP mouse model was analyzed.

A. Study Design

Sixty-six to seventy two mice were given 1.5 μg/mouse of rat anti-CD41 antibody (Ab) clone MWReg30 (BioLegend cat #133910) once daily for 4 days (on Days 1, 2, 3 and 4), intraperitoneally. Six to twelve mice were dosed in the same manner with a rat IgG1, k isotype control (BioLegend cat #400414). All mice were dosed once intravenously with saline control, IVIg, S1-IVIg, S2-IVIg, or desialylated-IVIg (Des-IVIg) at different doses 1 to 2 hours after the third anti-CD41 Ab injection (Table 4). Mice were bled on Day 4 (4 h after the forth anti-CD41 injection) and on Day 5 (24 h after the forth anti-CD41 Ab injection) to quantitate total platelet and reticulated platelet levels. To confirm that platelet depletion was successful, a subgroup of mice was bled on Day 3, prior to treatment.

TABLE 4

IVIg, S1-IVIg, S2-IVIg, and Des-IVIg dose response study details

| Group # | n | Induction (1.5 μg IP) 4 daily doses | Treatment Agent (200 uL IV) | Dose | Timing of Dosing | Blood Sampling |
|---|---|---|---|---|---|---|
| 1 | 6 | anti-CD41 | Saline | 200 μL | 1-2 h post 3. anti-CD41 dose | Day 3, 4 and Day 5 |
| 2 | 6 | Rat IgG1 | Saline | 200 μL | 1-2 h post 3. anti-CD41 dose | Day 4 and Day 5 |
| 3 | 8 | anti-CD41 | IVIg Gammagard | 0.5 g/kg | 1-2 h post 3. anti-CD41 dose | Day 4 and Day 5 |
| 4 | 8 | anti-CD41 | IVIg Gammagard | 1 g/kg | 1-2 h post 3. anti-CD41 dose | Day 4 and Day 5 |
| 5 | 8 | anti-CD41 | S1-IVIg | 0.5 g/kg | 1-2 h post 3. anti-CD41 dose | Day 4 and Day 5 |
| 6 | 8 | anti-CD41 | S1-IVIg | 1 g/kg | 1-2 h post 3. anti-CD41 dose | Day 4 and Day 5 |
| 7 | 8 | anti-CD41 | S2-IVIg | 0.5 g/kg | 1-2 h post 3. anti-CD41 dose | Day 4 and Day 5 |
| 8 | 8 | anti-CD41 | S2-IVIg | 1 g/kg | 1-2 h post 3. anti-CD41 dose | Day 4 and Day 5 |
| 9 | 8 | anti-CD41 | Des-IVIg | 0.5 g/kg | 1-2 h post 3. anti-CD41 dose | Day 4 and Day 5 |
| 10 | 8 | anti-CD41 | Des-IVIg | 1 g/kg | 1-2 h post 3. anti-CD41 dose | Day 4 and Day 5 |

B. Methods

ITP Induction in Mice:

In vivo studies were conducted using female C57BL/6 mice (18-22 g, Charles Rivers Labs, MA). All procedures were performed in compliance with the Animal Welfare Act and with the Guide for the Care and Use of Laboratory Animals.

Quantitation of Total Platelets:

Blood samples were collected by submandibular bleed into EDTA coated tubes, and then run on a VetScan Instrument for platelet level determination. Total platelet levels were analyzed using One-Way ANOVA with Dunnett's or Bonferroni's post-test.

Quantitation of Reticulated Platelets:

To evaluate and quantitate for the presence of reticulated (young) platelets which contain residual RNA, whole blood was sequentially stained for total platelets (anti-CD61) followed by staining for the RNA with thiazole orange (RNA-binding dye, commercially available as ReticCount Reagent from BD Biosciences). This analysis was performed for blood samples collected on Day 5.

Ten microliters of whole blood was transferred into the bottom of α 5 mL FACS tube. Five microliters of anti-mouse CD61-PE antibody (BD Biosciences) was added directly to the whole blood and samples were mixed thoroughly by pipetting. Samples were incubated at room temperature for 5 minutes in the dark. Two milliliters of ReticCount reagent (BD Biosciences) was added to each sample and samples incubated for a minimum of 30 minutes at room temperature.

Samples were acquired on a FACS Canto flow cytometer (BD Biosciences). Total platelets were identified by forward and side scatter characteristics of the cells and distinguished from erythrocytes by gating on CD61-PE positive events. A total 10,000 platelet events were recorded for each sample. Using FlowJo software, a gate was set on the reticulated platelets (CD61 positive and thiazole orange positive) using samples from isotype control treated mice to achieve a rate of 6-10% reticulated platelets (normal rate). The same gate was then applied to all subsequent samples and treatment groups to calculate percentages of reticulated and non-reticulated platelets. Total counts of reticulated and non-reticulated platelets for each sample were calculated by multiplying the total number of platelets measured in the VetScan Instrument by the percentage of the platelet fraction. Total reticulated and non-reticulated platelet levels were analyzed using One-Way ANOVA with Dunnett's or Bonferroni's post-test.

In addition to the overall platelet quantification using the VetScan Instrument, numbers of reticulated platelets were also determined using ReticCount, anti-CD61-PE labeled Ab and flow cytometry.

C. Results

The results of the IVIg, S1-IVIg, S2-IVIg, and Des-IVIg dose response study are shown in Table 5.

TABLE 5

Total, reticulated, and non-reticulated platelet counts ($10^9$/L) on Day 5

| | Disease Induction | | | | | | | | | |
|---|---|---|---|---|---|---|---|---|---|---|
| | Isotype Control (1.5 µg) | Anti-CD41 Ab (1.5 µg) | | | | | | | | |
| | Treatment | | | | | | | | | |
| | Saline | Saline | IVIg | | S1-IVIg | | S2-IVIg | | desialylated IVIg | |
| | | | Dose | | | | | | | |
| | | | 0.5 g/kg | 1 g/kg | 0.5 g/kg | 1 g/kg | 0.5 g/kg | 1 g/kg | 0.5 g/kg | 1 g/kg |
| n per group | 6 | 6 | 8 | 7 | 6 | 8 | 7 | 8 | 8 | 7 |
| Total Platelets × $10^9$/L [mean ± SD] | 733 ± 73 | 240 ± 200 | 282 ± 79 | 429 ± 116 | 355 ± 137 | 356 ± 89 | 362 ± 94 | 501 ± 102 | 224 ± 51 | 182 ± 78 |
| Reticulated Platelets × $10^9$/L [mean ± SD] | 70 ± 18 | 97 ± 24 | 109 ± 76 | 268 ± 84 | 196 ± 64 | 234 ± 81 | 304 ± 73 | 391 ± 86 | 175 ± 42 | 134 ± 56 |
| Non-Reticulated Platelets × $10^9$/L [mean ± SD] | 663 ± 64 | 143 ± 182 | 173 ± 49 | 161 ± 77 | 159 ± 85 | 122 ± 63 | 58 ± 41 | 111 ± 69 | 49 ± 32 | 48 ± 26 |

Example 3—Comparison of IVIg, S1-IVIg, S2-IVIg, and Des-IVIg in a Chronic ITP Mouse Model The effect of IVIg, S1-IVIg, S2-IVIg, and Des-IVIg in an anti-CD41 antibody mediated ITP mouse model was analyzed.

A. Study Design

Sixty-six to seventy two mice were given 1.5 µg/mouse of rat anti-CD41 antibody (Ab) clone MWReg30 (BioLegend cat #133910) once daily for 4 days (on Days 1, 2, 3 and 4), intraperitoneally. Six to twelve mice were dosed in the same manner with a rat IgG1, k isotype control (BioLegend cat #400414). All mice were dosed once intravenously with saline control, IVIg, S1-IVIg, S2-IVIg, or desialylated-IVIg (Des-IVIg at different doses 1 to 2 hours after the third anti-CD41 Ab injection (Table 6). Mice were bled on Day 4 (4 h after the forth anti-CD41 injection) and on Day 5 (24 h after the forth anti-CD41 Ab injection) to quantitate total platelet and reticulated platelet levels. To confirm that platelet depletion was successful, a subgroup of mice was bled on Day 3, prior to treatment. On Day 4 bone marrow cells were isolated to quantitate megakaryocytes.

B. Methods

ITP Induction in Mice:

In vivo studies were conducted using female C57BL/6 mice (18-22 g, Charles Rivers Labs, MA). All procedures were performed in compliance with the Animal Welfare Act and with the Guide for the Care and Use of Laboratory Animals.

Quantitation of Total Platelets:

Blood samples were collected by submandibular bleed into EDTA coated tubes, and then run on a VetScan Instrument for platelet level determination. Total platelet levels were analyzed using One-Way ANOVA with Dunnett's or Bonferroni's post-test.

Quantitation of Reticulated Platelets:

To evaluate and quantitate for the presence of reticulated (young) platelets which contain residual RNA, whole blood was sequentially stained for total platelets (anti-CD61) followed by staining for the RNA with thiazole orange (RNA-binding dye, commercially available as ReticCount Reagent from BD Biosciences). This analysis was performed for blood samples collected on Day 5.

Ten microliters of whole blood was transferred into the bottom of α 5 mL FACS tube. Five microliters of anti-mouse

TABLE 6

IVIg, S1-IVIg, S2-IVIg, and Des-IVIg comparison study details

| Group # | n | Induction (1.5 µg IP) 4 daily doses | Treatment Agent (200 uL IV) | Dose | Timing of Dosing | Blood Sampling |
|---|---|---|---|---|---|---|
| 1 | 12 | anti-CD41 | Saline | 200 µL | 1-2 h post 3. anti-CD41 dose | Day 3, Day 4, and Day 5 |
| 2 | 12 | Rat IgG1 | Saline | 200 µL | 1-2 h post 3. anti-CD41 dose | Day 4 and Day 5 |
| 3 | 12 | anti-CD41 | IVIg Gammagard | 1 g/kg | 1-2 h post 3. anti-CD41 dose | Day 4 and Day 5 |
| 4 | 12 | anti-CD41 | S1-IVIg | 1 g/kg | 1-2 h post 3. anti-CD41 dose | Day 4 and Day 5 |
| 5 | 12 | anti-CD41 | S2-IVlg | 1 g/kg | 1-2 h post 3. anti-CD41 dose | Day 4 and Day 5 |
| 6 | 12 | anti-CD41 | Des-IVIg | 1 g/kg | 1-2 h post 3. anti-CD41 dose | Day 4 and Day 5 |

CD61-PE antibody (BD Biosciences) was added directly to the whole blood and samples were mixed thoroughly by pipetting. Samples were incubated at room temperature for 5 minutes in the dark. Two milliliters of ReticCount reagent (BD Biosciences) was added to each sample and samples incubated for a minimum of 30 minutes at room temperature.

Samples were acquired on a FACS Canto flow cytometer (BD Biosciences). Total platelets were identified by forward and side scatter characteristics of the cells and distinguished from erythrocytes by gating on CD61-PE positive events. A total 10,000 platelet events were recorded for each sample. Using FlowJo software, a gate was set on the reticulated platelets (CD61 positive and thiazole orange positive) using samples from isotype control treated mice to achieve a rate of 6-10% reticulated platelets (normal rate). The same gate was then applied to all subsequent samples and treatment groups to calculate percentages of reticulated and non-reticulated platelets. Total counts of reticulated and non-reticulated platelets for each sample were calculated by multiplying the total number of platelets measured in the VetScan Instrument by the percentage of the platelet fraction. Total reticulated and non-reticulated platelet levels were analyzed using One-Way ANOVA with Dunnett's or Bonferroni's post-test.

resuspended at $1\times10^6$ cells/mL. Cytospin slides were prepared with 0.5 mL per slide. The slides were air-dried and stored at 80° C. until use.

After blocking, cells were stained with anti-CD41 (rat anti-mouse CD41; clone: MWReg30, cat #133910, Biolegend; diluted 1:150 in PBS contains 10% normal donkey serum) by immunohistochemistry using a BondMax instrument (Leica) and the Rat Polink-2 open kit protocol. Slides were counter stained with hematoxylin, mounted, and cover slipped.

Stained slides were imaged using a Vectra microscope system under 4× and 20× magnification. Images were spectrally unmixed, segmented, then quantified for megakaryocyte count as well as CD41 signal intensity using Inform software. Total, mean and maximum signals as well as signal area was calculated for each category. Data were normalized to total cell numbers and reported as total OD signal or per cell ratio. Data were transferred into Excel and Graph Pad Prism, graphed and analyzed for statistically significant differences.

C. Results

The results of the IVIg, S1-IVIg, S2-IVIg, and Des-IVIg comparison study are shown in Table 7.

TABLE 7

Total, reticulated, and non-reticulated platelet counts ($10^9$/L) on Day 5 and Megakaryocyte count in bone marrow cells (MK/$10^6$ BM cells) on Day 4

| | Disease Induction | | | | | |
|---|---|---|---|---|---|---|
| | Isotype Control (1.5 μg) | Anti-CD41 Ab (1.5 μg) | | | | |
| | Treatment | | | | | |
| | Saline | Saline | IVIg | S1-IVIg | S2-IVIg | Desialylated IVIg |
| | | | Dose | | | |
| | | | 1 g/kg | 1 g/kg | 1 g/kg | 1 g/kg |
| n per group | 6 | 6 | 6 | 6 | 6 | 6 |
| Total Platelets [mean ± SD] | 739 ± 84 | 277 ± 203 | 290 ± 113 | 563 ± 138 | 578 ± 209 | 220 ± 97 |
| Reticulated platelets [mean ± SD] | 61 ± 11 | 98 ± 57 | 131 ± 60 | 184 ± 34 | 261 ± 49 | 130 ± 46 |
| Non-Reticulated platelets [mean ± SD] | 679 ± 75 | 179 ± 168 | 159 ± 60 | 379 ± 133 | 318 ± 177 | 90 ± 56 |
| Megakaryocytes in Bone Marrow [mean ± SD] | 328 ± 132 | 323 ± 51 | 341 ± 162 | 360 ± 31 | 496 ± 115 | 372 ± 87 |

In addition to the overall platelet quantification using the VetScan Instrument, numbers of reticulated platelets were also determined using ReticCount, anti-CD61-PE labeled Ab and flow cytometry.

Quantitation of Megakaryocytes in the Bone Marrow:

On Day 4 (1 day after IVIg treatment and 4 h after the $4^{th}$ anti-CD41 antibody injection) of the study, bone marrow was extracted from one femur per mouse by using a syringe with α 25 gauge needle, flushing the bone shaft repeatedly with 0.5 mL of media. Cell suspensions were filtered through a nylon mesh and fixed in 4% paraformaldehyde for 15 minutes on ice. Cells were washed twice with PBS buffer containing 10% culture grade normal bovine serum, resuspended and counted using a ViCell cell counter. Cells were

Example 4—Comparison of IVIg, rFc, S1-rFc, S2-rFc, and Des-IVIg in a Chronic ITP Mouse Model The effect of IVIg, rFc, S1-rFc, S2-rFc, and Des-IVIg in an anti-CD41 antibody mediated ITP mouse model was analyzed.

A. Study Design

Sixty-six to seventy two mice were given 1.5 μg/mouse of rat anti-CD41 antibody (Ab) clone MWReg30 (BioLegend cat #133910) once daily for 4 days (on Days 1, 2, 3 and 4), intraperitoneally. Six to twelve mice were dosed in the same manner with a rat IgG1, k isotype control (BioLegend cat #400414). All mice were dosed once intravenously with saline control, IVIg, recombinant Fc (rFc), S1-rFc, S2-rFc, or Des-IVIg at different doses 1 to 2 hours after the third anti-CD41 Ab injection (Table 8). Mice were bled on Day 4 (4 h after the forth anti-CD41 injection) and on Day 5 (24 h after the forth anti-CD41 Ab injection) to quantitate total platelet and reticulated platelet levels. To confirm that platelet depletion was successful, a subgroup of mice was bled on Day 3, prior to treatment. On Day 5 bone marrow cells were isolated to quantitate megakaryocytes.

was then applied to all subsequent samples and treatment groups to calculate percentages of reticulated and non-reticulated platelets. Total counts of reticulated and non-reticulated platelets for each sample were calculated by multiplying the total number of platelets measured in the VetScan Instrument by the percentage of the platelet fraction. Total reticulated and non-reticulated platelet levels were analyzed using One-Way ANOVA with Dunnett's or Bonferroni's post-test.

TABLE 8

IVIg, rFc, S1-rFc, S2-rFc, and Des-IVIg comparison study details

| Group # | n | Induction (1.5 μg IP) 4 daily doses | Treatment Agent (200 uL IV) | Dose | Timing of Dosing | Blood Sampling |
|---|---|---|---|---|---|---|
| 1 | 12 | anti-CD41 | Saline | 200 μL | 1-2 h post 3. anti-CD41 dose | Day 3, Day 4, and Day 5 |
| 2 | 12 | Rat IgG1 | Saline | 200 μL | 1-2 h post 3. anti-CD41 dose | Day 4 and Day 5 |
| 3 | 12 | anti-CD41 | IVIg Gammagard | 1 g/kg | 1-2 h post 3. anti-CD41 dose | Day 4 and Day 5 |
| 4 | 12 | anti-CD41 | rFc | 0.3 g/kg | 1-2 h post 3. anti-CD41 dose | Day 4 and Day 5 |
| 5 | 12 | anti-CD41 | S1-rFc | 0.3 g/kg | 1-2 h post 3. anti-CD41 dose | Day 4 and Day 5 |
| 6 | 12 | anti-CD41 | S2-rFc | 0.3 g/kg | 1-2 h post 3. anti-CD41 dose | Day 4 and Day 5 |
| 7 | 12 | anti-CD41 | Des-IVIg | 1 g/kg | 1-2 h post 3. anti-CD41 dose | Day 4 and Day 5 |

B. Methods

ITP Induction in Mice:

In vivo studies were conducted using female C57BL/6 mice (18-22 g, Charles Rivers Labs, MA). All procedures were performed in compliance with the Animal Welfare Act and with the Guide for the Care and Use of Laboratory Animals.

Quantitation of Total Platelets:

Blood samples were collected by submandibular bleed into EDTA coated tubes, and then run on a VetScan Instrument for platelet level determination. Total platelet levels were analyzed using One-Way ANOVA with Dunnett's or Bonferroni's post-test.

Quantitation of Reticulated Platelets:

To evaluate and quantitate for the presence of reticulated (young) platelets which contain residual RNA, whole blood was sequentially stained for total platelets (anti-CD61) followed by staining for the RNA with thiazole orange (RNA-binding dye, commercially available as ReticCount Reagent from BD Biosciences). This analysis was performed for blood samples collected on Day 5.

Ten microliters of whole blood was transferred into the bottom of α 5 mL FACS tube. Five microliters of anti-mouse CD61-PE antibody (BD Biosciences) was added directly to the whole blood and samples were mixed thoroughly by pipetting. Samples were incubated at room temperature for 5 minutes in the dark. Two milliliters of ReticCount reagent (BD Biosciences) was added to each sample and samples incubated for a minimum of 30 minutes at room temperature.

Samples were acquired on a FACS Canto flow cytometer (BD Biosciences). Total platelets were identified by forward and side scatter characteristics of the cells and distinguished from erythrocytes by gating on CD61-PE positive events. A total 10,000 platelet events were recorded for each sample. Using FlowJo software, a gate was set on the reticulated platelets (CD61 positive and thiazole orange positive) using samples from isotype control treated mice to achieve a rate of 6-10% reticulated platelets (normal rate). The same gate In addition to the overall platelet quantification using the VetScan Instrument, numbers of reticulated platelets were also determined using ReticCount, anti-CD61-PE labeled Ab and flow cytometry.

Quantitation of Megakaryocytes in the Bone Marrow:

On Day 5 of the study (ITP-010; 2 days after IVIg treatment and 24 h after the $4^{th}$ anti-CD41 antibody injection), bone marrow was extracted from one femur per mouse by using a syringe with α 25 gauge needle, flushing the bone shaft repeatedly with 0.5 mL of media. Cell suspensions were filtered through a nylon mesh and fixed in 4% paraformaldehyde for 15 minutes on ice. Cells were washed twice with PBS buffer containing 10% culture grade normal bovine serum, resuspended and counted using a ViCell cell counter. Cells were resuspended at $1\times10^6$ cells/mL. Cytospin slides were prepared with 0.5 mL per slide. The slides were air-dried and stored at 80° C. until use.

After blocking, cells were stained with anti-CD41 (rat anti-mouse CD41; clone: MWReg30, cat #133910, Biolegend; diluted 1:150 in PBS contains 10% normal donkey serum) by immunohistochemistry using a BondMax instrument (Leica) and the Rat Polink-2 open kit protocol. Slides were counter stained with hematoxylin, mounted, and cover slipped.

Stained slides were imaged using a Vectra microscope system under 4× and 20× magnification. Images were spectrally unmixed, segmented, then quantified for megakaryocyte count as well as CD41 signal intensity using Inform software. Total, mean and maximum signals as well as signal area was calculated for each category. Data were normalized to total cell numbers and reported as total OD signal or per cell ratio. Data were transferred into Excel and Graph Pad Prism, graphed and analyzed for statistically significant differences.

C. Results

The results of IVIg, rFc, S1-rFc, S2-rFc, and Des-IVIg comparison study are shown in Table 9.

TABLE 9

Total, reticulated, and non-reticulated platelet counts ($10^9$/L) and Megakaryocyte count in bone marrow cells (MK/$10^6$ BM cells) on Day 5

| | Disease Induction | | | | | | |
|---|---|---|---|---|---|---|---|
| | Isotype Control (1.5 μg) | Anti-CD41 Ab (1.5 μg) | | | | | |
| | Treatment | | | | | | |
| | Saline | Saline | IVIg | rFc | S1-rFc | S2-rFc | Des IVIg |
| | | | Dose | | | | |
| | | | 1 g/kg | 0.3 g/kg | 0.3 g/kg | 0.3 g/kg | 1 g/kg |
| n per group | 6 | 6 | 6 | 6 | 6 | 6 | 6 |
| Total Platelets [mean ± SD] | 734 ± 124 | 189 ± 83 | 401 ± 103 | 277 ± 226 | 379 ± 198 | 369 ± 89 | 160 ± 67 |
| Reticulated platelets [mean ± SD] | 64 ± 10 | 73 ± 39 | 125 ± 42 | 116 ± 55 | 178 ± 60 | 234 ± 95 | 122 ± 56 |
| Non-Reticulated platelets [mean ± SD] | 670 ± 117 | 116 ± 70 | 277 ± 106 | 161 ± 191 | 201 ± 157 | 135 ± 46 | 38 ± 25 |
| Megakaryocytes in Bone Marrow [mean ± SD] | 126 ± 64 | 1.0 ± 0.7 | 275 ± 87 | 237 ± 57 | 218 ± 68 | 345 ± 44 | 81 ± 53 |

While the methods have been described in conjunction with various instances and examples, it is not intended that the methods be limited to such instances or examples. On the contrary, the methods encompass various alternatives, modifications, and equivalents, as will be appreciated by those of skill in the art.

What is claimed is:

1. A pharmaceutical preparation comprising sialylated intravenous immunoglobulin (IVIG), wherein at least 65% of branched glycans are sialylated on both the α 1,3 arm and the α 1,6 arm by way of NeuAc-α2,6-Gal terminal linkages; at least 60% of the branched glycans in the Fab domain are sialylated on both the α 1,3 arm and the α 1,6 arm by way of NeuAc-α 2,6-Gal terminal linkages; and at least 80% of the branched glycans in the Fc domain are sialylated on both the α 1,3 arm and the α 1,6 arm by the way of NeuAc-α 2,6-Gal terminal linkages;

wherein the sialylated IVIG is prepared by enzymatically sialylating IVIG in vitro via an ST6 sialyltransferase.

2. The preparation of claim 1, wherein the ST6 sialyltransferase is ST6Gal1.

3. The preparation of claim 1, wherein the ST6 sialyltransferase is a polypeptide with at least 70% overall sequence identity with one or more of SEQ ID NO:1, SEQ ID NO:2, or amino acid residues 95-416 of SEQ ID NO:3.

4. The preparation of claim 1, wherein the preparation is administered to a subject by parenteral administration, transnasal administration, transpulmonary administration, or transcutaneous administration.

5. The preparation of claim 4, wherein the preparation is systemically administered to a subject by intravenous injection, intramuscular injection, intraperitoneal injection, or subcutaneous injection.

6. The preparation of claim 4, wherein the preparation is locally administered to a subject by intravenous injection, intramuscular injection, intraperitoneal injection, or subcutaneous injection.

7. The preparation of claim 1, wherein the preparation is incorporated in a pharmaceutical composition further comprising a pharmaceutically acceptable vehicle or media.

8. The preparation of claim 1, wherein the preparation is formulated in a sterile composition for injection further comprising a pharmaceutically acceptable vehicle.

* * * * *

SEQUENCE LISTING

```
Sequence total quantity: 3
SEQ ID NO: 1           moltype = AA  length = 418
FEATURE                Location/Qualifiers
source                 1..418
                       mol_type = protein
                       organism = Homo sapiens
SEQUENCE: 1
MTRLTVLALL AGLLASSRAG SSPLLAMEWS HPQFEKLEGG GSGGGSGGSW SHPQFEKHAH  60
AHSRKDHLIH NVHKEEHAHA HNKELGTAVF QGPMRRAIRG RSFQVWNKDS SSKNLIPRLQ  120
KIWKNYLSMN KYKVSYKGPG PGIKFSAEAL RCHLRDHVNV SMVEVTDFPF NTSEWEGYLP  180
KESIRTKAGP WGRCAVVSSA GSLKSSQLGR EIDDHDAVLR FNGAPTANFQ QDVGTKTTIR  240
LMNSQLVTTE KRFLKDSLYN EGILIVWDPS VYHSDIPKWY QNPDYNFFNN YKTYRKLHPN  300
QPFYILKPQM PWELWDILQE ISPEEIQPNP PSSGMLGIII MMTLCDQVDI YEFLPSKRKT  360
DVCYYYQKFF DSACTMGAYH PLLYEKNLVK HLNQGTDEDI YLLGKATLPG FRTIHCPG    418

SEQ ID NO: 2           moltype = AA  length = 375
FEATURE                Location/Qualifiers
source                 1..375
                       mol_type = protein
                       organism = Homo sapiens
SEQUENCE: 2
GSYYDSFKLQ TKEFQVLKSL GKLAMGSDSQ SVSSSSTQDP HRGRQTLGSL RGLAKAKPEA  60
SFQVWNKDSS SKNLIPRLQK IWKNYLSMNK YKVSYKGPGP GIKFSAEALR CHLRDHVNVS  120
MVEVTDFPFN TSEWEGYLPK ESIRTKAGPW GRCAVVSSAG SLKSSQLGRE IDDHDAVLRF  180
NGAPTANFQQ DVGTKTTIRL MNSQLVTTEK RFLKDSLYNE GILIVWDPSV YHSDIPKWYQ  240
NPDYNFFNNY KTYRKLHPNQ PFYILKPQMP WELWDILQEI SPEEIQPNPP SSGMLGIIIM  300
MTLCDQVDIY EFLPSKRKTD VCYYYQKFFD SACTMGAYHP LLYEKNLVKH LNQGTDEDIY  360
LLGKATLPGF RTIHC                                                   375

SEQ ID NO: 3           moltype = AA  length = 402
FEATURE                Location/Qualifiers
source                 1..402
                       mol_type = protein
                       organism = Homo sapiens
SEQUENCE: 3
MIHTNLKKKF SYFILAFLLF ALICVWKKGS YEALKLQAKE FQVTKSLEKL AIGSGSQSTS  60
ASIKQDSKPG SQVLSHLRVT AKVKPQSPYQ VWDKNSSSKN LNPRLQKILK NYLSMNKYKV  120
SYKGPGPGVK FSVEALRCHL RDRVNVSMIE ATDFPFNTTE WEGYLPKENF RTKAGPWHRC  180
```

-continued

| | |
|---|---|
| AVVSSAGSLK SSHLGKEIDS HDAVLRFNGA PVADFQQDVG MKTTIRLMNS QLITTEKQFL | 240 |
| KDSLYNEGIL IVWDPSLYHA DIPNWYKKPD YNFFETYKSY RKLYPSQPFY ILRPQMPWEL | 300 |
| WDIIQEIAPD RIQPNPPSSG MLGIIIMMTL CDQVDVYEFL PSKRKTDVCY YHQKFFDSAC | 360 |
| TMGAYHPLLF EKNMVKQLNE GTDEDIYIFG KATLSGFRTI HC | 402 |